United States Patent
Oelke et al.

(10) Patent No.: US 11,007,222 B2
(45) Date of Patent: May 18, 2021

(54) T CELL COMPOSITIONS WITH IMPROVED PHENOTYPIC PROPERTIES

(71) Applicant: NexImmune, Inc., Gaithersburg, MD (US)

(72) Inventors: Mathias Oelke, Gaithersburg, MD (US); Kristi Jones, Gaithersburg, MD (US); Sojung Kim, Gaithersburg, MD (US); Lauren Suarez, Gaithersburg, MD (US); Ken Carter, Gaithersburg, MD (US); Scott Carmer, Gaithersburg, MD (US); Dan Bednarik, Gaithersburg, MD (US); Vineetha Edavana, Gaithersburg, MD (US); Emily Lu, Gaithersburg, MD (US)

(73) Assignee: NEXIMMUNE, INC., Gaithersburg, MD (US)

( * ) Notice: Subject to any disclaimer, the term of this patent is extended or adjusted under 35 U.S.C. 154(b) by 0 days.

(21) Appl. No.: 16/707,309

(22) Filed: Dec. 9, 2019

(65) Prior Publication Data

US 2020/0215115 A1    Jul. 9, 2020

Related U.S. Application Data

(63) Continuation of application No. 16/678,366, filed on Nov. 8, 2019.

(60) Provisional application No. 62/867,499, filed on Jun. 27, 2019, provisional application No. 62/821,031, filed on Mar. 20, 2019, provisional application No. 62/757,467, filed on Nov. 8, 2018.

(51) Int. Cl.
| | |
|---|---|
| *A61K 35/17* | (2015.01) |
| *C07K 14/73* | (2006.01) |
| *C07K 14/705* | (2006.01) |
| *A61P 35/00* | (2006.01) |
| *C07K 14/725* | (2006.01) |
| *C07K 16/28* | (2006.01) |
| *A61K 35/12* | (2015.01) |

(52) U.S. Cl.
CPC ............. *A61K 35/17* (2013.01); *A61P 35/00* (2018.01); *C07K 14/7051* (2013.01); *C07K 14/70514* (2013.01); *C07K 14/70517* (2013.01); *C07K 16/2815* (2013.01); *A61K 2035/122* (2013.01); *A61K 2035/124* (2013.01)

(58) Field of Classification Search
CPC ............. A61K 35/17; A61K 2035/122; A61K 2035/124; A61P 35/00; C07K 14/7051
See application file for complete search history.

(56) References Cited

U.S. PATENT DOCUMENTS

| | | | |
|---|---|---|---|
| 6,015,884 A | 1/2000 | Schneck et al. | |
| 6,140,113 A | 10/2000 | Schneck et al. | |
| 6,268,411 B1 | 7/2001 | Schneck et al. | |
| 6,352,694 B1 | 3/2002 | June et al. | |
| 6,448,071 B1 | 9/2002 | Schneck et al. | |
| 6,458,354 B1 | 10/2002 | Schneck et al. | |
| 6,734,013 B2 | 5/2004 | Schneck et al. | |
| 6,797,514 B2 | 9/2004 | Berenson et al. | |
| 6,867,041 B2 | 3/2005 | Berenson et al. | |
| 6,905,874 B2 | 6/2005 | Berenson et al. | |
| 7,541,184 B2 | 6/2009 | Berenson et al. | |
| 7,572,631 B2 | 8/2009 | Berenson et al. | |
| 7,670,781 B2 | 3/2010 | Riley et al. | |
| 7,973,137 B1 | 7/2011 | Schneck et al. | |
| 7,977,095 B2 | 7/2011 | Bonyhadi et al. | |
| 9,763,985 B2 | 9/2017 | Volk et al. | |
| 9,974,808 B2 | 5/2018 | Bonini et al. | |
| 10,098,939 B2 | 10/2018 | Schneck et al. | |
| 10,131,876 B2 | 11/2018 | Kaiser et al. | |
| 10,351,824 B2 | 7/2019 | Rooney et al. | |
| 2002/0131960 A1 | 9/2002 | Sadelain et al. | |
| 2004/0115216 A1 | 6/2004 | Schneck et al. | |
| 2007/0141704 A1 | 6/2007 | Nicolette et al. | |
| 2010/0008920 A1 | 1/2010 | Schneck et al. | |
| 2010/0284965 A1 | 11/2010 | Fahmy et al. | |
| 2011/0070185 A1* | 3/2011 | Cai .......................... | C07K 7/08 424/85.2 |

(Continued)

FOREIGN PATENT DOCUMENTS

| | | |
|---|---|---|
| JP | 2011036263 | 2/2011 |
| WO | 2009094273 | 7/2009 |

(Continued)

OTHER PUBLICATIONS

Walz et al Bood 126: 1203-1213, 2015 (Year: 2015).*
Bacher, et al., "Flow-Cytometric Analysis of Rare Antigen-Specific T Cells", Cytometry Part A 83A: 692701, 2013.
Barrett, et al., "Relapse after allogeneic stem cell transplantation", Expert Rev Hematol. Aug. 2010, 3(4): 429-441.
Chiu et al., "HLA-Ig Based Artificial Antigen Presenting Cells for Efficient ex vivo Expansion of Human CTL." Journal of Visualized Experiments, 2011, 50, e2801, pp. 1-5.

(Continued)

*Primary Examiner* — Lei Yao
(74) *Attorney, Agent, or Firm* — Morgan, Lewis & Bockius LLP

(57) ABSTRACT

The present invention provides an isolated cell composition, which in some embodiments is suitable for adoptive immunotherapy, as well as methods of manufacturing the cell compositions and methods of treatment with the cell compositions. The composition comprises, in a pharmaceutically acceptable carrier, at least about $10^6$ CD8+ T cells specific for target peptide antigen(s), which comprises T memory stem ($T_{SCM}$) cells. In various embodiments, the composition is from about 1% to about 100% T memory stem cells, providing for a robust and durable adoptive therapy, as well as providing for T cell engineering advances.

21 Claims, 14 Drawing Sheets

Specification includes a Sequence Listing.

(56) References Cited

U.S. PATENT DOCUMENTS

| | | |
|---|---|---|
| 2011/0256147 A1 | 10/2011 | Oelke et al. |
| 2011/0293637 A1 | 12/2011 | Hacohen et al. |
| 2013/0202548 A1 | 8/2013 | Rowan et al. |
| 2014/0370099 A1 | 12/2014 | Green et al. |
| 2015/0366991 A1 | 12/2015 | Schneck et al. |
| 2016/0000829 A1 | 1/2016 | June et al. |
| 2016/0051698 A1 | 2/2016 | Schneck et al. |
| 2016/0237137 A1 | 8/2016 | Webb et al. |
| 2017/0051252 A1 | 2/2017 | Morgan et al. |
| 2017/0107490 A1 | 4/2017 | Maeurer |
| 2017/0246277 A1* | 8/2017 | Schneck .............. B03C 1/288 |
| 2019/0062706 A1 | 2/2019 | Almaasbak et al. |
| 2019/0134092 A1 | 5/2019 | Knaus et al. |

FOREIGN PATENT DOCUMENTS

| | | |
|---|---|---|
| WO | 2015153788 | 10/2015 |
| WO | 2017068421 | 4/2017 |
| WO | 2017161092 | 9/2017 |
| WO | WO2019060558 | * 3/2019 |

OTHER PUBLICATIONS

Dal Porto et al., "A soluble divalent class I major histocompatibility complex molecule inhibits alloreactive T cells at nanomolar concentrations", Immunology: Proc. Natl. Acad. Sci., 1993, vol. 90, pp. 6671-6675.

De La Pena et al., "Artificial exosomes as tools for basic and clinical immunology", J. Immunol. Methods, 2009, vol. 344, No. 2, pp. 121-132.

Dennis, "Off by a Wisker", Nature. 2006, vol. 442, pp. 739-741.

Duan et al., "Preparation of Immunomagnetic Iron-Dextran Nanoparticles and Application in Rapid Isolation of *E. coli*", World Journal Gastroenterol., 2005, vol. 11, No. 24 pp. 3660-3664.

Garber, et al., "Adoptive T-cell therapy for Leukemia", Molecular and Cellular Therapies 2014, vol. 2, No. 25, pp. 1-22.

Grant et al., Cell therapies for hematological malignancies: don't forget non-gene-modified t cells!, Blood Reviews, 2017, pp. 1-22.

Greten, et al., "Development and Use of Multimeric Major Histocompatibility Complex Molecules," Clinical and Diagnostic Laboratory Immunology, 2002, pp. 216-220.

Greten et al., "MHC-Ig Dimeric Molecules Dimers—MHC-Ig dimeric molecules for the analysis of antigen-specific T cell responses", D. Nagorsen and F.M. Marincola (eds.), 2005, Analyzing. T Cell Responses, pp. 227-238.

Gura, "Systems for Identifying New Drugs are Often Faulty", Science, 1997, vol. 278, pp. 1041-1042.

Huang, et al., "Detection, phenotyping, and quantification of antigen-specific T cells using a peptide-MHC dodecamer", PNAS, 2016, pp. E1890-E1897.

International Search Report and Written Opinion for International Application No. PCT/US2018-015971, dated Jan. 29, 2019, 10 pages.

Ito et al., "Magnetic Force-Based Mesenchymal Stem Cell Expansion Using Antibody-Conugated Magnetoliposomes", J. Biomed. Mater. Res. B Appl. Biomater., 2005, vol. 2, pp. 320-327.

Kim et al., "Single Step Isolation and Activation of Primary CD3+ T Lymphocytes using Alcohol-Dispersed Electrospun Magnetic Nanofibers", Nano Letter, 2012, vol. 12 No. 8, pp. 4018-4024.

Lam, et al., "Broadly-specific Cytotoxic T Cells Targeting Multiple HIV Antigens are Expanded From HIV+ Patients: Implications for Immunotherapy," Molecular Therapy, 2015, vol. 23, No. 2, pp. 387-395.

Lo et al., "Selective Activation of Antigen-Experienced T Cells by Anti-CD3 Constrained on Nanoparaticles", J. Immunol., 2013, vol. 191, No. 10, pp. 5107-5114.

Maus et al., "HLA Tetramer-Based Artificial Antigen-Presenting Cells for Stimulation of CD4+ T cells", Clin. Immunol., 2003, vol. 106, No. 1, pp. 16-22.

Montagna et al., "Feasibility and safety of adoptive immunotherapy with ex vivo-generated autologous, cytotoxic T lymphocytes in patients with solid tumor", Cytotherapy, 2012, vol. 14, pp. 80-90.

Oelke et al., "Ex vivo induction and expression of antigen-specific cytotoxic T cells by HLA-Ig-coated artificial antien-presenting cells", Nat. Med., 2003, vol. 5, pp. 619-624.

Oelke et al., "Overview of a HLA-Ig based "Lego-like system" for T cell monitoring, modulation and expansion," Immunologic Research, 2010, vol. 47, No. 1-3, pp. 248-256.

Perica et al., "Magnetic Field-Induced T Cell Receptor Clustering by Nanoparticles Enhances T Cell Activation and Stimulates Antitumor Activity", ACS Nano, 2014, vol. 8, No. 3, pp. 2252-2260.

Perica, et al., "Enrichment and Expansion with Nano-Artificial Antigen Presenting Cells for Adoptive Immunotherapy", ACS Nano., 2015, vol. 9, No. 7, pp. 6861-6871.

Perica, et al., "Nanoscale artificial antigen presenting cells for T cell immunitherapy", Nanomedicine, Epub., 2013, vol. 10 No. 1 pp. 119-129.

Pollack et al., "Tetramer guided, cell sorter assisted production of clinical grade autologous NY-ESO-1 specific CD8+ T cells," Journal for ImmunoTherapy of Cancer, 2014, vol. 2 No. 36, pp. 1-10.

Quintarelli, et al., "Cytotoxic T lymphocytes directed to the preferentially expressed antigen of melanoma (PRAME) target chronic myeloid leukemia," Blood, 2008, vol. 112, No. 5, pp. 1876-1885.

Reagan-Shaw et al., Dose Translation From Animal to Human Studies Revisited, FASEB J, 2007, 22: 659-661.

Rosenberg et al., "Adoptive cell transfer as personalized immunotherapy for human cancer," Science, 2015, vol. 348, issue 6230, pp. 62-68.

Saengruengrit et al., The combined magnetic field and iron oxide-PLGA composite particles: Effective protein antigen delivery an dimmune stimulation in dentritic cells, J. Colloid and Interface Science, 2018, vol. 520, pp. 101-111.

Seruga et al. Failures in Phase III: Causes and Consequences:, Clin Cancer Res, 2015, vol. 21 pp. 4554-4560.

Steenblock et al., "A comprehensive platform for Ex Vivo T-cell expansion based on biodegradable polymeric artificial antigen-presenting cells," Molecular Therapy, 2008, vol. 16, No. 4, pp. 765-772.

Thompson et al., A Phase I Trial of CD3/CD28-activated T Cells (Xcellerated T Cells) and Interleutkin-2 in Patients with Metastatic Renal Cell Carcinoma, Clin. Cancer Res., 2003, vol. 9 pp. 3562-3570.

Turtle, et al., "Artificial Antigen Presenting Cells for use in Adoptive Immunotherapy," Cancer J., 2010, vol. 16, No. 4, pp. 374-381.

Ugel et al., "In vivo Administration of Artificial Antigen-Presenting Cells Activates Low-Avidity T Cells for Treatment of Cancer", Cancer Res., 2009, vol. 69, No. 24 pp. 9376-9384.

Weber, et al., Generation of Tumor Antigen-Specific T Cell Lines from Pediatric Patients with Acute Lymphoblastic Leukemia—Implications for Immunotherapy, Clin Cancer Res; 2013, vol. 19, No. 18, pp. 5079-5091.

Wölfl, et al., "Antigen-specific activation and cytokine-facilitated expansion of naive, human CD8+ T cells," Nat Protoc., 2014, vol. 9, No. 4, pp. 950-966.

Yao, et al., "Increased PRAME-Specific CTL Killing of Acute Myeloid Leukemia Cells by Either a Novel Histone Deacetylase Inhibitor Chidamide Alone or Combined Treatment with Decitabine," PLOS One, 2013, vol. 8, No. 8, pp. 1-13.

Yee et al., "Isolation of High Avidity Melanoma-Reactive CTL from Heterogeneous Populations Using Peptide-MHC Tetramers", the Journal of Immunology, 1999, vol. 162, pp. 2227-2234.

* cited by examiner

SEQUENCE LISTING

<160> NUMBER OF SEQ ID NOS: 56

<210> SEQ ID NO 1
<211> LENGTH: 9
<212> TYPE: PRT
<213> ORGANISM: Homo sapiens

<400> SEQUENCE: 1

Arg Met Phe Pro Asn Ala Pro Tyr Leu
1               5

<210> SEQ ID NO 2
<211> LENGTH: 9
<212> TYPE: PRT
<213> ORGANISM: Homo sapiens

<400> SEQUENCE: 2

Cys Met Thr Trp Asn Gln Met Asn Leu
1               5

<210> SEQ ID NO 3
<211> LENGTH: 9
<212> TYPE: PRT
<213> ORGANISM: Homo sapiens

<400> SEQUENCE: 3

Val Leu Asp Phe Ala Pro Pro Gly Ala

```
<210> SEQ ID NO 4
<211> LENGTH: 9
<212> TYPE: PRT
<213> ORGANISM: Homo sapiens

<400> SEQUENCE: 4

Ser Leu Gly Glu Gln Gln Tyr Ser Val
1               5

<210> SEQ ID NO 5
<211> LENGTH: 9
<212> TYPE: PRT
<213> ORGANISM: Homo sapiens

<400> SEQUENCE: 5

Val Leu Asp Gly Leu Asp Val Leu Leu
1               5

<210> SEQ ID NO 6
<211> LENGTH: 9
<212> TYPE: PRT
<213> ORGANISM: Homo sapiens

<400> SEQUENCE: 6

Asn Leu Thr His Val Leu Tyr Pro Val
1               5

<210> SEQ ID NO 7
<211> LENGTH: 10
<212> TYPE: PRT
<213> ORGANISM: Homo sapiens

<400> SEQUENCE: 7

Ser Leu Tyr Ser Phe Pro Glu Pro Glu Ala
1               5                   10

<210> SEQ ID NO 8
<211> LENGTH: 10
<212> TYPE: PRT
<213> ORGANISM: Homo sapiens

<400> SEQUENCE: 8

Ala Leu Tyr Val Asp Ser Leu Phe Phe Leu
1               5                   10

<210> SEQ ID NO 9
<211> LENGTH: 9
<212> TYPE: PRT
<213> ORGANISM: Homo sapiens

<400> SEQUENCE: 9

Ser Leu Leu Gln His Leu Ile Gly Leu
1               5

<210> SEQ ID NO 10
<211> LENGTH: 10
<212> TYPE: PRT
<213> ORGANISM: Homo sapiens

<400> SEQUENCE: 10

Glu Leu Thr Leu Gly Glu Phe Leu Lys Leu
1               5                   10
```

```
<210> SEQ ID NO 11
<211> LENGTH: 10
<212> TYPE: PRT
<213> ORGANISM: Homo sapiens

<400> SEQUENCE: 11

Leu Asp Arg Glu Arg Ala Lys Asn Lys Ile
1               5                   10

<210> SEQ ID NO 12
<211> LENGTH: 9
<212> TYPE: PRT
<213> ORGANISM: Homo sapiens

<400> SEQUENCE: 12

Phe Leu Asp Arg Phe Leu Ser Cys Met
1               5

<210> SEQ ID NO 13
<211> LENGTH: 11
<212> TYPE: PRT
<213> ORGANISM: Homo sapiens

<400> SEQUENCE: 13

Ser Leu Ile Ala Ala Ala Ala Phe Cys Leu Ala
1               5                   10

<210> SEQ ID NO 14
<211> LENGTH: 9
<212> TYPE: PRT
<213> ORGANISM: Homo sapiens

<400> SEQUENCE: 14

Tyr Ile Ser Pro Trp Ile Leu Ala Val
1               5

<210> SEQ ID NO 15
<211> LENGTH: 9
<212> TYPE: PRT
<213> ORGANISM: Homo sapiens

<400> SEQUENCE: 15

Tyr Leu Phe Pro Gln Leu Ile Ser Val
1               5

<210> SEQ ID NO 16
<211> LENGTH: 9
<212> TYPE: PRT
<213> ORGANISM: Homo sapiens

<400> SEQUENCE: 16

Gly Leu Val Gly Leu Ile Phe Ala Val
1               5

<210> SEQ ID NO 17
<211> LENGTH: 9
<212> TYPE: PRT
<213> ORGANISM: Homo sapiens

<400> SEQUENCE: 17

Ser Leu Phe Val Leu Gly Leu Phe Leu
1               5

<210> SEQ ID NO 18
```

```
<211> LENGTH: 9
<212> TYPE: PRT
<213> ORGANISM: Homo sapiens

<400> SEQUENCE: 18

Ser Leu Leu Met Trp Ile Thr Gln Ala
1               5

<210> SEQ ID NO 19
<211> LENGTH: 10
<212> TYPE: PRT
<213> ORGANISM: Homo sapiens

<400> SEQUENCE: 19

Ala Leu Ser Pro Ala Ser Ser Arg Ser Val
1               5                   10

<210> SEQ ID NO 20
<211> LENGTH: 9
<212> TYPE: PRT
<213> ORGANISM: Homo sapiens

<400> SEQUENCE: 20

Cys Leu Gly Gly Leu Leu Thr Met Val
1               5

<210> SEQ ID NO 21
<211> LENGTH: 9
<212> TYPE: PRT
<213> ORGANISM: Homo sapiens

<400> SEQUENCE: 21

Phe Leu Tyr Ala Leu Ala Leu Leu Leu
1               5

<210> SEQ ID NO 22
<211> LENGTH: 9
<212> TYPE: PRT
<213> ORGANISM: Homo sapiens

<400> SEQUENCE: 22

Gly Leu Cys Thr Leu Val Ala Met Leu
1               5

<210> SEQ ID NO 23
<211> LENGTH: 9
<212> TYPE: PRT
<213> ORGANISM: Homo sapiens

<400> SEQUENCE: 23

Tyr Val Leu Asp His Leu Ile Val Val
1               5

<210> SEQ ID NO 24
<211> LENGTH: 10
<212> TYPE: PRT
<213> ORGANISM: Homo sapiens

<400> SEQUENCE: 24

Leu Leu Asp Phe Val Arg Phe Met Gly Val
1               5                   10

<210> SEQ ID NO 25
<211> LENGTH: 9
<212> TYPE: PRT
```

```
<213> ORGANISM: Homo sapiens

<400> SEQUENCE: 25

Tyr Leu Gln Gln Asn Trp Trp Thr Leu
1               5

<210> SEQ ID NO 26
<211> LENGTH: 9
<212> TYPE: PRT
<213> ORGANISM: Homo sapiens

<400> SEQUENCE: 26

Ile Tyr Val Leu Val Met Leu Val Leu
1               5

<210> SEQ ID NO 27
<211> LENGTH: 9
<212> TYPE: PRT
<213> ORGANISM: Homo sapiens

<400> SEQUENCE: 27

Thr Tyr Pro Val Leu Glu Glu Met Phe
1               5

<210> SEQ ID NO 28
<211> LENGTH: 9
<212> TYPE: PRT
<213> ORGANISM: Homo sapiens

<400> SEQUENCE: 28

Asp Tyr Asn Phe Val Lys Gln Leu Phe
1               5

<210> SEQ ID NO 29
<211> LENGTH: 9
<212> TYPE: PRT
<213> ORGANISM: Homo sapiens

<400> SEQUENCE: 29

Arg Tyr Ser Ile Phe Phe Asp Tyr Met
1               5

<210> SEQ ID NO 30
<211> LENGTH: 9
<212> TYPE: PRT
<213> ORGANISM: Homo sapiens

<400> SEQUENCE: 30

Thr Tyr Ser Ala Gly Ile Val Gln Ile
1               5

<210> SEQ ID NO 31
<211> LENGTH: 9
<212> TYPE: PRT
<213> ORGANISM: Homo sapiens

<400> SEQUENCE: 31

Arg Pro Pro Ile Phe Ile Arg Arg Leu
1               5

<210> SEQ ID NO 32
<211> LENGTH: 9
<212> TYPE: PRT
<213> ORGANISM: Homo sapiens
```

<400> SEQUENCE: 32

Gln Pro Arg Ala Pro Ile Arg Pro Ile
1               5

<210> SEQ ID NO 33
<211> LENGTH: 13
<212> TYPE: PRT
<213> ORGANISM: Homo sapiens

<400> SEQUENCE: 33

Arg Pro Gln Gly Gly Ser Arg Pro Glu Phe Val Lys Leu
1               5                   10

<210> SEQ ID NO 34
<211> LENGTH: 9
<212> TYPE: PRT
<213> ORGANISM: Homo sapiens

<400> SEQUENCE: 34

Gly Ile Leu Gly Phe Val Phe Thr Leu
1               5

<210> SEQ ID NO 35
<211> LENGTH: 9
<212> TYPE: PRT
<213> ORGANISM: Homo sapiens

<400> SEQUENCE: 35

Gln Pro Glu Trp Phe Arg Asn Val Leu
1               5

<210> SEQ ID NO 36
<211> LENGTH: 9
<212> TYPE: PRT
<213> ORGANISM: Homo sapiens

<400> SEQUENCE: 36

Ser Pro Ile Val Pro Ser Phe Asp Met
1               5

<210> SEQ ID NO 37
<211> LENGTH: 9
<212> TYPE: PRT
<213> ORGANISM: Homo sapiens

<400> SEQUENCE: 37

Gln Tyr Asp Pro Val Ala Ala Leu Phe
1               5

<210> SEQ ID NO 38
<211> LENGTH: 9
<212> TYPE: PRT
<213> ORGANISM: Homo sapiens

<400> SEQUENCE: 38

Val Tyr Ala Leu Pro Leu Lys Met Leu
1               5

<210> SEQ ID NO 39
<211> LENGTH: 9
<212> TYPE: PRT
<213> ORGANISM: Homo sapiens

<400> SEQUENCE: 39

Ala Tyr Ala Gln Lys Ile Phe Lys Ile
1               5

<210> SEQ ID NO 40
<211> LENGTH: 10
<212> TYPE: PRT
<213> ORGANISM: Homo sapiens

<400> SEQUENCE: 40

Thr Pro Arg Val Thr Gly Gly Gly Ala Met
1               5                   10

<210> SEQ ID NO 41
<211> LENGTH: 11
<212> TYPE: PRT
<213> ORGANISM: Homo sapiens

<400> SEQUENCE: 41

Arg Pro His Glu Arg Asn Gly Phe Thr Val Leu
1               5                   10

<210> SEQ ID NO 42
<211> LENGTH: 9
<212> TYPE: PRT
<213> ORGANISM: Homo sapiens

<400> SEQUENCE: 42

Ile Leu Ser Leu Glu Leu Met Lys Leu
1               5

<210> SEQ ID NO 43
<211> LENGTH: 9
<212> TYPE: PRT
<213> ORGANISM: Homo sapiens

<400> SEQUENCE: 43

Ser Leu Glu Glu Asn Ile Val Ile Leu
1               5

<210> SEQ ID NO 44
<211> LENGTH: 9
<212> TYPE: PRT
<213> ORGANISM: Homo sapiens

<400> SEQUENCE: 44

Lys Leu Leu Glu Tyr Ile Glu Glu Ile
1               5

<210> SEQ ID NO 45
<211> LENGTH: 9
<212> TYPE: PRT
<213> ORGANISM: Homo sapiens

<400> SEQUENCE: 45

Lys Leu Gln Glu Glu Leu Asn Lys Val
1               5

<210> SEQ ID NO 46
<211> LENGTH: 9
<212> TYPE: PRT
<213> ORGANISM: Homo sapiens

<400> SEQUENCE: 46

Lys Leu Lys Gly Lys Glu Ala Glu Leu
1               5

```
<210> SEQ ID NO 47
<211> LENGTH: 9
<212> TYPE: PRT
<213> ORGANISM: Homo sapiens

<400> SEQUENCE: 47

Val Leu Gln Glu Leu Asn Val Thr Val
1               5

<210> SEQ ID NO 48
<211> LENGTH: 10
<212> TYPE: PRT
<213> ORGANISM: Homo sapiens

<400> SEQUENCE: 48

Glu Leu Ala Gly Ile Gly Ile Leu Thr Val
1               5                   10

<210> SEQ ID NO 49
<211> LENGTH: 9
<212> TYPE: PRT
<213> ORGANISM: Homo sapiens

<400> SEQUENCE: 49

Ile Met Asp Gln Val Pro Phe Ser Val
1               5

<210> SEQ ID NO 50
<211> LENGTH: 9
<212> TYPE: PRT
<213> ORGANISM: Homo sapiens

<400> SEQUENCE: 50

Ser Leu Leu Met Trp Ile Thr Gln Cys
1               5

<210> SEQ ID NO 51
<211> LENGTH: 9
<212> TYPE: PRT
<213> ORGANISM: Homo sapiens

<400> SEQUENCE: 51

Ser Leu Leu Met Trp Ile Thr Gln Ala
1               5

<210> SEQ ID NO 52
<211> LENGTH: 9
<212> TYPE: PRT
<213> ORGANISM: Homo sapiens

<400> SEQUENCE: 52

Asn Leu Val Pro Met Val Ala Thr Val
1               5

<210> SEQ ID NO 53
<211> LENGTH: 9
<212> TYPE: PRT
<213> ORGANISM: Homo sapiens

<400> SEQUENCE: 53

Ile Ser Pro Trp Ile Leu Ala Val Leu
1               5
```

```
<210> SEQ ID NO 54
<211> LENGTH: 8
<212> TYPE: PRT
<213> ORGANISM: Homo sapiens

<400> SEQUENCE: 54

Val Tyr Pro Glu Gly Ser Ser Leu
1               5

<210> SEQ ID NO 55
<211> LENGTH: 9
<212> TYPE: PRT
<213> ORGANISM: Homo sapiens

<400> SEQUENCE: 55

Ile Phe Ala Val Cys Leu Val Gly Phe
1               5

<210> SEQ ID NO 56
<211> LENGTH: 9
<212> TYPE: PRT
<213> ORGANISM: Homo sapiens

<400> SEQUENCE: 56

Leu Phe Val Leu Gly Leu Phe Leu Trp
1               5
```

US 11,007,222 B2

T CELL COMPOSITIONS WITH IMPROVED PHENOTYPIC PROPERTIES

PRIORITY

This application claims the benefit of U.S. Provisional Application No. 62/757,467, filed Nov. 8, 2018, U.S. Provisional Application No. 62/821,031, filed Mar. 20, 2019, and the benefit of U.S. Provisional Application No. 62/867,499, filed Jun. 27, 2019, each which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, filed Mar. 4, 2020 is named "NEX-011C1_SequenceListing_ST25.txt" and is 12,288 bytes in size.

BACKGROUND

Immunotherapy has become a cornerstone in cancer therapy that includes a broad array of strategies aiming to unleash, direct, and boost the patient's own immune system through adoptive transfer of expanded naturally circulating or genetically engineered cytotoxic lymphocytes. Despite recent advances in the field, current adoptive immunotherapies encounter several challenges. For example, many adoptive immunotherapies cannot generate a sufficient level of engineered cytotoxic lymphocytes of clinical or therapeutic value from peripheral blood, or have an inability to uniformly engineer effector cells, or cannot provide a sustained, long lasting therapeutic effect for the patient, resulting in tumor re-occurrence and other complications. Thus, there is a significant need for cell compositions that provide for more effective, durable, and safer adoptive immunotherapy options, including for patients suffering from leukemia or lymphoma (including acute or chronic leukemia), as well as other patients that could benefit from adoptive immunotherapy. In various aspects and embodiments, the present invention addresses these needs.

SUMMARY OF THE INVENTION

In various aspects and embodiments, the invention provides an isolated cell composition, which is suitable for adoptive immunotherapy and/or genetic engineering of T cells. The invention further provides methods of manufacturing the cell compositions and methods of treatment with the cell compositions. The composition comprises, in a pharmaceutically acceptable carrier, at least about $10^6$ CD8+ T cells specific for target peptide antigen(s), and which comprises T memory stem ($T_{SCM}$) cells. In various embodiments, the CD8+ T cells are at least about 1% T memory stem cells. In some embodiments, T memory stem cells are isolated, thereby preparing a composition substantially comprising T memory stem cells (e.g., 70% to 100% $T_{SCM}$). The compositions of the invention, by virtue of the presence of significant levels of $T_{SCM}$, can provide for a robust and durable adoptive therapy. The cell composition need not comprise T cells expressing a chimeric antigen receptor or a recombinant TCR, and therefore, in various embodiments, provides an alternative to these technologies that often produce more exhausted T cell phenotypes and less durable responses and greater toxicities. In other embodiments, the $T_{SCM}$ are used to recombinately express a chimeric antigen receptor or heterologous TCR, thereby preparing engineered T cells with high proliferative capacity and less exhausted phenotype.

In various embodiments, the cell composition comprises at least 1%, or at least 15% T memory stem cells and about $10^6$ CD8+ T cells specific for the target peptide antigens, or at least about $10^7$, or at least about $10^8$, or at least about $10^9$, or at least about $10^{10}$ CD8+ T cells specific for the target peptide antigens, to provide robust destruction of target cells and a long persistence in vivo. For example, for treatment of acute myelogenous leukemia (AML) or myelodysplastic syndrome, the cell composition may comprise T cells specific for WT1, PRAME, Survivin, and Cyclin A1 peptide antigens, among others.

In various embodiments, the cell composition comprises from about 1% to about 50% T memory stem cells, or from about 5% to about 25% T memory stem cells. In various embodiments, the T cells are at least 5% T memory stem cells, or the T cells are at least about 10% T memory stem cells, or the T cells are at least 20% T memory stem cells, or at least 25% T memory stem cells, which provides an adoptive immunotherapy composition with significant proliferative potential, as well as immune-reconstitution capacity and longevity.

In various embodiments, greater than 95% of the CD8+ T cells in the composition comprise a memory phenotype. In various embodiments, the memory phenotype comprises, in addition to $T_{SCM}$, one or more (or all) of central memory T cells ($T_{CM}$), effector memory T cells ($T_{EM}$), and effector memory RA+ T cells ($T_{EMRA}$). In some embodiments, at least 80% of the memory phenotype is $T_{SCM}$, $T_{CM}$, and $T_{EM}$.

In various embodiments, the CD8+ T cells in the composition comprise, in addition to $T_{SCM}$, central memory and effector memory T cells. In various embodiments, the T cells in the composition (and/or the T cells specific for the target antigens) are at least about 30% central or effector memory T cells, or in some embodiments are at least about 50% central or effector memory T cells, or in some embodiments are at least about 70% central or effector memory cells, or in some embodiments are at least about 80% central or effector memory T cells, or in some embodiments are at least about 90% central or effector memory T cells. In some embodiments, the CD8+ T cells specific for the one or more target antigens are at least 50% central and effector memory T cells, or in some embodiments are at least 80% central and effector memory T cells. In some embodiments, the combination of $T_{SCM}$ and $T_{CM}$ is from about 40% to about 70% of the CD8+ T cells.

In some embodiments, the cell composition comprises less than about 20%, or less than about 10%, terminally differentiated memory T cells (e.g., $T_{EMRA}$ cells), and less than about 30% naive cells, or in some embodiments less than about 15%, or in some embodiments less than about 5%, or in some embodiments less than 1.5% naïve cells. The cell phenotype disclosed herein can be created and/or controlled using an enrichment and expansion process with paramagnetic artificial Antigen Presenting Cells (aAPCs) and a recombinant T cell growth factor cocktail.

In various embodiments, the cell composition is at least about 70%, or at least about 80%, or at least about 90% CD8+ or CD4− T cells (e.g., CD3+ CD8+ or CD3+ CD4− cells). For example, the isolated cell composition may be characterized by having less than about 10%, or less than about 5% CD4+ T cells. When expanding CD8+ T cells ex vivo, CD4+ cells have a tendency to overgrow the CD8+ cells and compete for growth signals, and exogenous CD4+ cells are not necessary for a robust and durable in vivo response.

In various embodiments, the antigen-specific T cells display a polyfunctional phenotype upon activation. In some embodiments, at least 10% of the CD8+ T cells, or in some embodiments at least 20% of the CD8+ T cells, or in some embodiments at least 40% of the CD8+ T cells, display a polyfunctional phenotype upon activation. For example, upon activation the T cells are positive for two or more of: intracellular staining for IL-2, IFN-γ production, production of TNF-α, and CD107A. In various embodiments, at least 20% of the antigen-specific T cells display at least two of these markers. In various embodiments, at least 20% of the antigen-specific T cells display at least three of these markers, or in some embodiments all four of these markers. In various embodiments, at least 5% of the CD8+ T cells are multi-antigenic, meaning the CD8+ T cells are capable of responding to multiple tumor or viral antigens in vitro or in vivo.

In various embodiments, the cell composition further comprises γδ T cells. γδ T cells have a distinctive T-cell receptor (TCR) on their surface. γδ T cells may have a role in recognition of lipid antigens and phospho antigens, and can provide anti-pathogen and anti-tumor mechanisms that are not HLA-dependent. Further, γδ T cells can provide help to the CD8+ cells. Clinical significance of γδ T cells in the context of hematopoietic stem cell transplantation (HSCT) has been observed, and in particular, higher frequencies of γδ T cells after transplantation were associated with favorable outcomes.

Cell compositions in accordance with various embodiments can be prepared by an enrichment and expansion process. In some embodiments, CD8+ cells are enriched that are specific for the target antigen(s) (e.g., tumor associated antigens or viral-associated antigens). This cell population, even when predominately naive cells in the source lymphocytes, can be rapidly expanded in culture to arrive at the cell compositions described herein. Enrichment can take place using paramagnetic beads to positively select cell populations, and which can have the added advantage of activating naive cells and other T cell populations due to potent magnetic clustering of T cell surface receptors. For example, paramagnetic beads or nanoparticles may contain monomeric or multimeric (e.g., dimeric) HLA ligands presenting peptide antigens, along with a co-stimulation signal on the same or different particles, such as an agonist for CD28 (e.g., an antibody agonist of CD28). In some embodiments, CD28+ cells are also enriched, which can be simultaneous with antigen-specific enrichment.

In various embodiments, the target peptide antigens are tumor or cancer associated antigens, including tumor-derived, tumor-specific antigens, and neoantigens. T cells specific for tumor-associated antigens are often very rare, and in many cases undetectable, in the peripheral blood of healthy individuals. This is often a distinction observed between viral-specific and tumor antigen-specific T cells.

In some embodiments, the target peptide antigens include at least one that is associated with or derived from a pathogen, such as a viral, bacterial, fungal, or parasitic pathogen. For example, at least one peptide antigen may be associated with HIV, hepatitis (e.g., B, C, or D) CMV, Epstein-Barr virus (EBV), influenza, herpes virus (e.g., HSV 1 or 2, or varicella zoster), and Adenovirus. CMV, for example, is the most common viral pathogen found in organ transplant patients and is a major cause of morbidity and mortality in patients undergoing bone marrow or peripheral blood stem cell transplants. Viral activation is known to be implicated in cancer biology.

In still other embodiments, the cell composition comprises T cells specific for tumor-associated antigens, with pathogen-associated antigen specific T cells provided as bystander cells. Other bystander cells include γδ T cells. Specifically, by enriching with HLA-peptide and anti-CD28, bystander cells will be enriched, and expanded, particularly when using a T cell growth factor cocktail that can drive some non-specific expansion of these cells without antigen-specific activation. In these embodiments, while a large portion of the composition are T cells specific for the target peptides (e.g., from 5% to 75%), remaining T cells (from about 0.25% to about 25%) provide some reconstitution of the immune system for common pathogens, which is particularly beneficial after transplant or beneficial in cancers with viral etiology.

Some embodiments employ T cell growth factors during expansion, which affect proliferation and/or differentiation of T cells. Particularly useful cytokines include MIP-1β, IL-1β, IL-2, IL-4, IL-6, IL-7, IL-10, IL-21, and INF-γ. In these or other embodiments, the cells are expanded in culture in the presence of a cytokine cocktail comprising one, two, or three cytokines selected from MIP-1β, IL-1β, and IL-6. In some embodiments, the cytokines further comprise IL-10. In some embodiments, the growth factors comprise or consist essentially of IL-2, IL-4, IL-6, INF-γ, and IL-1β. Cells can be expanded in culture from 1 to 4 weeks, such as from about 10 to about 21 days.

In other aspects, the invention provides methods for manufacturing the cell compositions, including by enrichment and expansion with aAPCs as described herein. Specifically, after depletion of CD4+ cells from source lymphocytes (e.g., from a healthy donor or from a patient in need of adoptive immunotherapy), antigen-specific CD8+ T cells are enriched for T cells specific for the target peptide antigens, as well as CD28+ cells in some embodiments. Target cells can be enriched using nanoparticle or microparticle aAPCs, such as superparamagnetic nanoparticles that activate T cells ex vivo by magnetic field induced clustering of cell surface receptors. Other materials, including latex or other polymeric-based nanoparticles can also be used to cluster cell surface receptors (without magnetic-induced clustering). Enriched T cells can then be rapidly expanded ex vivo, including with the use of reconstituted T cell growth factors (e.g., comprising factors selected from MIP-1β, IL-1β, IL-2, IL-4, IL-6, IL-7, IL-10, IL-12, IL-15, IL-21, IFN-γ). In some embodiments, the cells are expanded in culture in the presence of one, two, or three cytokines selected from MIP-1β, IL-1β, IL-6, and IL-10. In some embodiments, the growth factors comprise or consist essentially of IL-2, IL-4, IL-6, INF-γ, and IL-1β. In various embodiments, these cytokines are used in conjunction with artificial or natural antigen presenting cells to expand antigen specific T cells.

In other aspects, the invention provides methods for adoptive cell therapy, including methods for treating a patient with cancer, and/or patients that have undergone allogeneic stem cell transplantation, with or without lympho-deleting therapy, cyto-reductive therapy, immunomodulatory therapy (prior to administration of the cell therapy). The cell therapy may be further provided with or without cytokine support post treatment. In some embodiments, the patient has a hematological cancer, which in some embodiments has relapsed after allogeneic stem cell transplantation. In some embodiments, the patient has acute myelogenous leukemia (AML) or myelodysplastic syndrome. For example, in some embodiments, the cell composition comprises T cells specific for WT1, PRAME, Survivin, and Cyclin A1 peptide antigens. However, in other embodiments, the cancers include various types of solid tumors, including carcinomas, sarcomas, and lymphomas. Exemplary target peptide antigens are described herein.

In some embodiments, the patient has an infectious disease or is at risk for an infectious disease. For example, patients that have undergone HSCT are at particular risk for infectious disease, given the immunocompromised state. Infectious diseases that can be treated or prevented include those caused by bacteria, viruses, prions, fungi, parasites, helminths, etc. Such diseases include AIDS, hepatitis B/C, CMV infection, Epstein-Barr virus (EBV) infection, influenza, herpes virus infection (including shingles), and adenovirus infection.

In still other embodiments, the invention provides a method for making a population of γδ T cells. The method comprises expanding a population of cells comprising γδ T cells in the presence of two or more of IL-2, IL-4, IL-6, INF-γ, and IL-1β. Before expansion, the population of cells comprises less than about 20% or less than about 10% or less than about 8% γδ T cells. In some embodiments, the population of cells is CD28 enriched. In some embodiments, the population of cells is CD4+ depleted. Expansion of cells in culture can take place as described herein, such as for 1 to 4 weeks. γδ T cells can be separated from other cells using known methods, such as cell sorting, and can be provided as a cell composition for adoptive transfer or research use, and alternatively may be modified to express one or more heterologous or engineered genes, such as a heterologous or engineered T cell receptor (e.g., αβ TCR), including a chimeric antigen receptor (CAR).

Other aspects and embodiments will be apparent from the following detailed description.

DESCRIPTION OF THE FIGURES

FIG. 4A shows the AML antigen-specific CD8+ T cell population after enrichment but prior to expansion at Day 0 (top), and after expansion at Day 14 (bottom). $T_{CM}$=central memory T cells (CD62L+, CD45RA−); $T_N$=naïve T cells (CD62L+, CD45RA+); $T_{EM}$=effector memory T cells (CD62L−, CD45RA−); $T_{EMRA}$=effector memory RA+T cells (CD62L−, CD45RA+); $T_{SCM}$=T memory stem cells (CD62L+, CD45RA+, CD95+). FIG. 4B shows the memory T cell phenotypes for $T_{SCM}$, $T_{CM}$, $T_{EM}$, and $T_{EMRA}$ on day 14 after AML-specific enrichment and expansion for AML specific antigens $WT1_{37-45, 126-134}$, $PRAME_{425}$, Cyclin $A1_{227-235, 341-351}$.

In FIG. 5A (bottom), the graph shows the percentage of T cells expressing IL-2, TNF-α, IFN-γ, and CD107A. In FIG. 5A, the T cells were stimulated by non-specific stimulation of peptide-pulsed T2 cells. In FIG. 5B, a graph is shown of T cell mediated tumor specific killing of AML cell line U266 at two effector to target (E:T) ratios, 10:1 (left bar) and 20:1 (right bar), using CTLs generated from fresh PBMCs of healthy donors with AML specific antigens $WT1_{37-45, 126-134}$, $PRAME_{425}$, and Cyclin $A1_{227-235, 341-351}$.

DETAILED DESCRIPTION OF THE INVENTION

Figure 1:
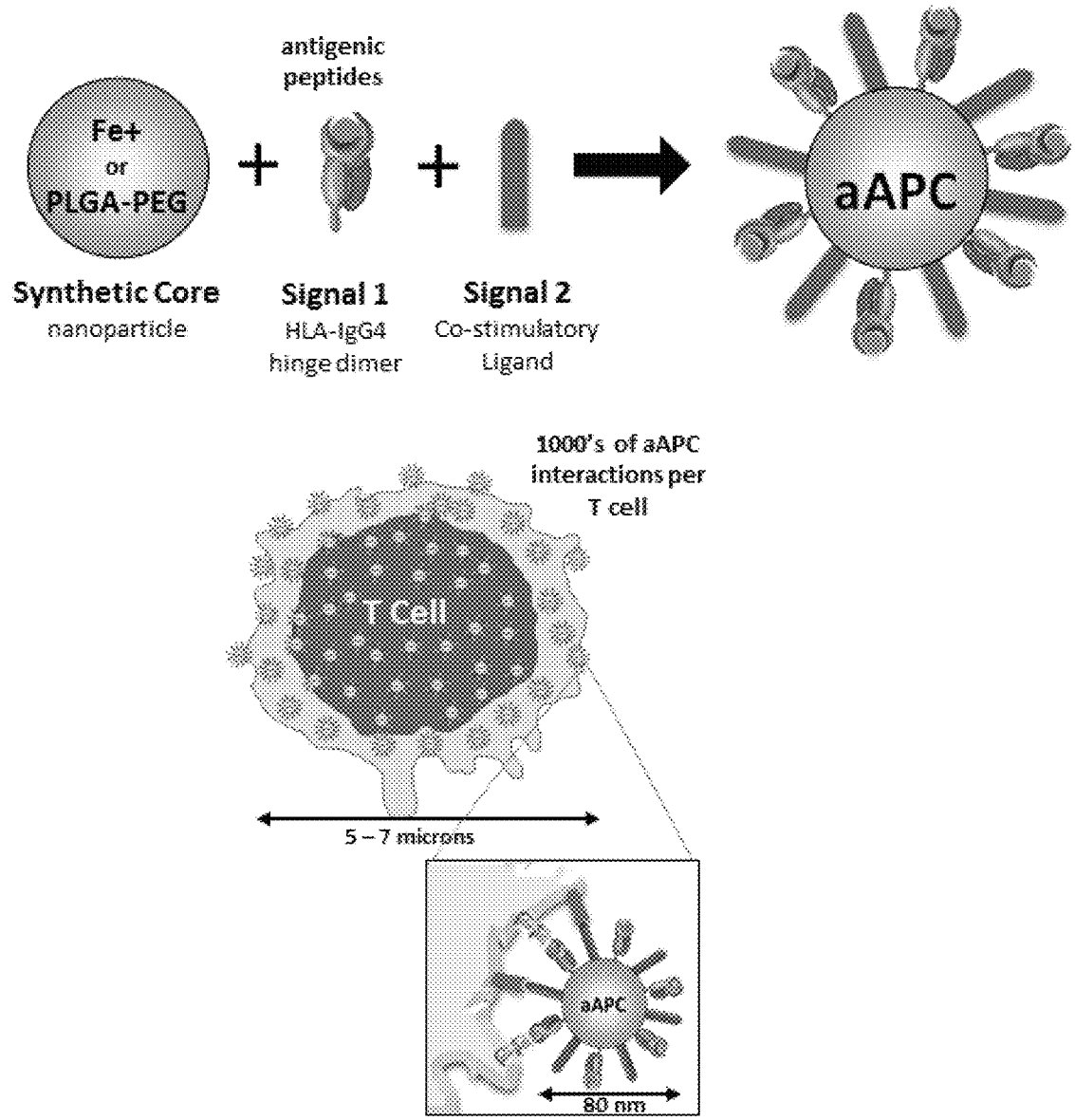
FIG. 1 is an image showing the Artificial Immune Modulation (AIM) platform for the generation of CD8+ antigen specific T cells.

T cell memory is heterogeneous in composition, comprised of stable, resting, phenotypically-distinct subsets of surface markers capable of unique functional responses upon stimulation. Subsets related by differentiation include central memory T cells ($T_{CM}$), effector memory T cells ($T_{EM}$), effector memory RA+ T cells ($T_{EMRA}$), and T memory stem cells ($T_{SCM}$). Memory T cells develop when antigen-specific naive CD4+ or CD8+ T cells become activated upon antigen exposure and subsequently undergo proliferative expansion and differentiation. Accordingly, persistent memory is essential for long-term protection against infections and malignancies. Only the $T_{SCM}$ subset cells of T memory cells have been shown to differentiate into central memory T cells ($T_{CM}$), effector memory ($T_{EM}$), and terminal effector T cells ($T_{TE}$). However, T memory stem cells are scarce and represent a small proportion of circulating lymphocytes. Generating clinically relevant amounts of T memory stem cells, e.g., for adoptive immunotherapy, is currently not feasible. Therefore, technologies are needed that can generate, expand, and enable the redirection of $T_{SCM}$ cells against cancer and infectious disease antigens.

Disclosed herein are isolated cell compositions having at least about $10^6$ CD8+ T cells specific for target peptide antigen(s), and which comprise $T_{SCM}$ cells. The $T_{SCM}$ cells of the present disclosure express surface markers that are similar to naïve T cells, but express elevated levels of the CD95 surface marker. Such $T_{SCM}$ cells are the least differentiated and expanded memory subset. Compared to other memory subsets, the $T_{SCM}$ cells of the present disclosure demonstrate an enormous proliferative capability, are capable of reconstituting the full repertoire of memory and effector T cells, and are a long-term, stable population of cells endowed with superior homeostatic and differentiation capabilities. Thus, the compositions disclosed herein having at least about $10^6$ CD8+ T cells specific for target peptide antigen(s), and which comprise $T_{SCM}$ cells provide a highly effective anti-tumor composition that can generate, expand, and enable the redirection of $T_{SCM}$ cells against cancer cells at clinically relevant amounts for therapeutic applications.

In various aspects and embodiments, the invention provides an isolated cell composition, as well as methods of manufacturing the cell compositions and methods of treatment with the cell compositions. In some embodiments, the cell compositions are used for adoptive cell therapy. The composition comprises, in a pharmaceutically acceptable carrier, at least about $10^6$ CD8+ T cells specific for target peptide antigen(s), and which comprise $T_{SCM}$ cells. In various embodiments, the CD8+ T cells are at least about 1% $T_{SCM}$ cells. In some embodiments, $T_{SCM}$ cells are isolated, thereby preparing a composition comprising nearly 100% T memory stem cells (e.g., at least 90% $T_{SCM}$ cells). In some embodiments, a composition of from about 70% to about 100% T memory stem cells is created. The compositions of the invention, by virtue of the presence of significant levels of T memory stem cells, provide for a robust and durable adoptive therapy. The cell composition need not comprise T cells expressing a chimeric antigen receptor (CAR) or a recombinant TCR, and therefore, in various embodiments, provides an alternative to these technologies that often produce more exhausted T cell phenotypes and less durable responses. In other embodiments, the $T_{SCM}$ are used to recombinately express a chimeric antigen receptor or heterologous TCR (e.g., αβ TCR or γδ TCR), thereby preparing engineered T cells with high proliferative capacity and less exhausted phenotype than previously described. Thus, the $T_{SCM}$ cells can be used for engineering T cells with CARs or heterologous TCRs.

As used herein, the term "target peptide antigen(s)" or "target antigens" refers to peptide antigens employed ex vivo to enrich and/or expand the desired CD8+ cell population, for example in connection with artificial Antigen Presenting Cell (aAPC) or professional Antigen Presenting Cell (pAPC) platforms (e.g., dendritic cells). The aAPCs or pAPCs are employed to activate and expand CTLs from donor or patient lymphocytes. In some embodiments, the target peptide antigens are peptide epitopes loaded onto aAPCs for ex vivo enrichment and expansion of specific CD8+ T cells. Thus, the term "specific for the target peptide antigen" means that the T cell is antigen experienced with the target antigen.

In various embodiments, the cell composition comprises at least about $10^6$ CD8+ T cells specific for the target peptide antigens, or at least about $10^7$ CD8+ T cells specific for the target peptide antigens, or at least about $10^8$, at least about $10^9$, or at least about $10^{10}$ CD8+ T cells specific for the target peptide antigens, to provide robust destruction of target cells. In some embodiments, the cell composition contains from $1\times10^7$ to $1\times10^9$ CD8+ T cells specific for the target antigens, or in some embodiments from $5\times10^7$ to $5\times10^8$ CD8+ T cells specific for the target antigens. For example, the composition can comprise from about $5\times10^5$ to about $5\times10^6$ cells per ml, in a volume of from 50 to 200 ml. In certain embodiments, the volume of the composition is ≤100 ml (e.g., from 50 to 100 ml). The cells of the composition in various embodiments are at least 70% viable or at least about 80% or about 90% viable, and provided in a sterile medium, which may be a cryoprotectant medium (e.g., 10% DMSO). The medium can be an aqueous medium suitable for intravenous infusion, e.g., including water and electrolytes. An exemplary medium is PLASMALYTE.

Disclosed herein is a cell composition comprising CD8+ cytotoxic lymphocytes (CTLs) and memory T cells. The CTLs of the present disclosure include the following T cell populations: naive, T memory stem cell, central memory, effector memory, and terminally differentiated memory cells. In accordance with embodiments of the invention, T cells specific for the target antigens include a significant amount of $T_{SCM}$ cells. In various embodiments, the T cells specific for the target antigens further include central memory T cells and effector memory T cells. The cell composition provides a durable response, including in vivo persistence of antigen-specific T cells for at least about 6 months, or at least about 12 months, or at least about 18 months, or at least about two years in some embodiments.

A naive T cell has differentiated in bone marrow, and successfully undergone the positive and negative processes of central selection in the thymus. A naive T cell is considered mature and, unlike activated or memory T cells, has not encountered its cognate antigen. Naive T cells can be characterized by the surface expression of L-selectin (CD62L) and the absence of activation surface markers. In the naive state, T cells are generally quiescent and non-dividing. In accordance with this disclosure, naive T cells are defined as CD62L+ and CD45RA+.

Memory T cells include T memory stem cells ($T_{SCM}$), central memory and effector memory T cells. Memory T cells have previously responded to their cognate antigen. At a second encounter with the cognate antigen, memory T cells can reproduce to mount a faster and stronger immune response. Memory T cells include at least T memory stem cells, effector memory T cells, and central memory T cells. Memory T cell subtypes are long-lived and can quickly expand to large numbers of effector T cells upon re-exposure to their cognate antigen.

T memory stem cells ($T_{SCM}$) are defined herein as CD45RA+ and as having at least the following surface markers: CD62L+, CD45RA+, and CD95+. In some embodiments, the T memory stem cells disclosed herein are CD62L+, CD45RA+, CD95+ and may have one or more of the following surface markers: CD28+, CD27+, CXCR3+ CD11a+, IL-2Rβ+, CD58+, and CD57−. In some embodiments, the T memory stem cells comprise cells that are CD62L+, CD45RA+, CD28+, CD27+, and CD95+. In some embodiments, the T memory stem cells comprise cells that are CD62L+, CD45RA+, CD95+ and CXCR3+. In some embodiments, the T memory stem cells comprise cells that are CD62L+, CD45RA+, CD95+ and CD11a+. In some embodiments, the T memory stem cells comprise cells that are CD62L+, CD45RA+, CD95+ and IL-2Rβ+. In some embodiments, the T memory stem cells comprise cells that are CD62L+, CD45RA+, CD95+ and CD58+. In some embodiments, the T memory stem cells comprise cells that are CD62L+, CD45RA+, CD95+ and CD57−. This memory subpopulation has the stem cell-like capacity for self-renewal, as well as the multipotent capacity to reconstitute the memory and effector T cell subpopulations. $T_{SCM}$ cells typically represent a small fraction of circulating T lymphocytes (e.g., >5%), and have the ability to proliferate rapidly and release inflammatory cytokines in response to antigen re-exposure. Accordingly, $T_{SCM}$ cells are a subset of the memory T cell subpopulation. The $T_{SCM}$ cells can be created and/or controlled using, as disclosed herein, an enrichment and expansion process with paramagnetic artificial Antigen Presenting Cells (aAPCs) and a recombinant T cell growth factor cocktail.

In accordance with this disclosure, central memory T cells ($T_{CM}$ cells) are defined herein as CD62L+ and CD45RA−. This memory subpopulation is commonly found in the lymph nodes and in the peripheral circulation. Effector memory T cells ($T_{EM}$ cells) are defined herein as CD62L− and CD45RA−. These memory T cells lack lymph node-homing receptors and are thus found in the peripheral circulation and tissues. TEMRA stands for terminally differentiated effector memory cells re-expressing CD45RA ($T_{emra}$). These cells do not have the capacity to divide, and are CD62L− and CD45RA+.

T central memory ($T_{CM}$) cells display a capacity for self-renewal, and in accordance with embodiments of the invention, are also important for obtaining a long-lived effect. $T_{EM}$ cells also have some capacity for self-renewal, and strongly express genes essential to the cytotoxic function. $T_{EMRA}$ cells also provide robust cytotoxic function, but do not display a capacity for self-renewal.

The compositions in various embodiments comprise CTLs that are substantially composed of $T_{SCM}$, $T_{CM}$ and $T_{EM}$ cells to balance duration of the effect versus potent destruction of the malignancy or other target cells. For example, in some embodiments these cells make up at least about 75% or at least about 80% or at least about 90% of the memory phenotype.

In various embodiments, the T cells in the composition are at least about 30% central and effector memory cells, or at least about 40% central or effector memory cells, or at least about 50% central or effector memory T cells, or in some embodiments are at least about 70% central or effector memory cells, or at least about 80% central or effector memory T cells, or at least about 90% central or effector memory T cells.

The cell composition comprises less than about 20% terminally differentiated memory T cells (e.g., $T_{EMRA}$ cells), or less than about 10% or less than about 5% or less than about 4% terminally differentiated memory T cells in some embodiments. In various embodiments, the CD8+ T cells contain no more than about 30% naive cells, or in some embodiments, no more than about 15% naive cells, or no more than about 10% naive cells, or no more than about 5% naive cells, or no more than about 4% naive cells, or no more than about 3% naive cells, or no more than about 2% naive cells, or no more than about 1.5%, or no more than about 1% naive cells.

In various embodiments, the CD8+ T cells contain from about 1% to about 100% T memory stem cells, or in some embodiments, from about 1% to about 50% T memory stem cells, or in some embodiments, from about 1% to about 25% T memory stem cells, or from about 5% to about 25% T memory stem cells, or from about 5% to about 15% T memory stem cells. (i.e., with the total of naïve, $T_{SCM}$, $T_{CM}$, $T_{EM}$ $T_{emra}$ cells as 100%)

In some embodiments, the $T_{SCM}$ and $T_{CM}$ cells make up from about 30% to about 80% of the memory phenotype, or in some embodiments about 40% to about 80% of the memory phenotype, or in some embodiments about 40% to about 70% of the memory phenotype.

In various embodiments, the T cells specific for the target antigens are at least about 30% central and effector memory cells, or at least about 40% central or effector memory cells, or at least about 50% central or effector memory T cells, or in some embodiments are at least about 70% central or effector memory cells, or at least about 80% central or effector memory T cells, or at least about 90% central or effector memory T cells. In some embodiments, these memory cells are about 10:90 to about 90:10 central to effector memory cells. In some embodiments, these T cells are from about 25:75 to about 75:25 central to effector memory cells. In some embodiments, the memory T cells are from about 40:60 to about 60:40 central to effector memory T cells. The T cells specific for the target antigen(s) are less than about 20% terminally differentiated memory T cells (e.g., TEMRA cells), or less than about 10% or less than about 5% or less than about 4% terminally differentiated memory T cells. In various embodiments, the T cells specific for target antigens contain no more than about 30% naive cells, or in some embodiments, no more than about 20% naive cells, or in some embodiments, no more than about 15% naive cells, or no more than about 10% naive cells, or no more than about 5% naive cells, or no more than about 2%, or 1.5%, or 1% naive cells. In various embodiments, the antigen-specific T cells contain from about 1% to about 100% T memory stem cells, or in some embodiments, from about 1% to about 50% T memory stem cells, or in some embodiments, from about 5% to about 25% T memory stem cells, or from about 5% to about 15% T memory stem cells. These memory T cells can be created by the enrichment and expansion process with paramagnetic artificial Antigen Presenting Cells (aAPCs). Populations containing predominately $T_{SCM}$ cells can be created be further isolating or enriching for $T_{SCM}$ cells using known techniques, including magnetic enrichment or cell sorting.

In various embodiments, the cell composition is at least 90% T cells, or at least 95% T cells, or at least 98%, or at least 99% T cells. For purposes of this disclosure, T cells are characterized by CD3+ cells. The T cells are generally CD8+ or CD4−. As used herein, the terms "CD8+" and "CD4−" are interchangeable unless stated otherwise. For example, the isolated cell composition may be characterized by having less than about 10%, or less than about 5% CD4+ T cells, or in some embodiments, less than about 2%, less than about 1.5%, or less than about 1% CD4+ T cells. When expanding CD8+ T cells ex vivo, CD4+ cells have a tendency to overgrow the CD8+ cells and compete for growth signals, and exogenous CD4+ T cells are not necessary for a robust and durable response upon adoptive transfer.

It has been described that the presence of polyfunctional CD4+ and CD8+ T cells correlates with response to cancer vaccine therapy with peptide neoantigens. Ott P A, et al., *An immunogenic personal neoantigen vaccine for patients with melanoma*, Nature 547(7662):217-221 (2017). CD4+ and CD8+ T cells are further described as being important for mediating tumor cell destruction. See, Tran E, *Cancer immunotherapy based on mutation-specific CD4+ T cells in a patient with epithelial cancer.* Science 344, 641-645 (2014); Sahin U, et al., *Personalized RNA mutanome vaccines mobilize poly-specific therapeutic immunity against cancer,* Nature 547(7662):222-226 (2017). With respect to this disclosure, it is believed that adoptive cell compositions need only provide substantial numbers of antigen-specific CD8+ T cells, particularly where the phenotype can support a robust and durable response, and particularly where the antigen-specific CD8+ T cells are provided in sufficient numbers.

In various embodiments, the cell composition is substantially CD28+. For example, in various embodiments, the cell composition is at least about 25%, or at least about 50%, or at least about 75%, or at least about 90% CD28+.

In various embodiments, the antigen-specific T cells display a polyfunctional phenotype upon activation. For example, upon activation the T cells are positive for two or more of: intracellular staining for IL-2, which is a marker for proliferation and memory; IFN-γ production, which activates other T cells, and induces memory and upregulation of MHC); production of TNF-α, a pro-inflammatory marker; and CD107A, which is a marker for granzyme release and cytotoxic activity. In various embodiments, at least 20%, at least 30%, at least 40%, at least 50%, at least 60%, at least 70%, or at least 80% of the antigen-specific T cells display at least three of these markers. In various embodiments, at least 20%, at least 30%, at least 40%, at least 50%, at least 60%, at least 70%, or at least 80% of the antigen-specific T cells display all four of these markers. In some embodiments, polyfunctionality is assessed or quantified using target killing assays, which assess the ability of CD8+ cytotoxic T cells to lyse target cells presenting the peptide antigen in complex with MHC.

In various embodiments, the cell composition further comprises γδ T cells. γδ T cells have a distinctive T-cell receptor (TCR) on their surface. In contrast to αβ T cells, γδ T cells have a TCR that is made up of one γ chain and one δ chain. γδ T cells are believed to not require antigen processing and major-histocompatibility-complex (MHC) presentation of peptide epitopes for activation. γδ T cells may have a role in recognition of lipid antigens and phospho antigens, and can play a role in anti-viral and anti-tumor protection. See, Kalyan and Kabelitz, *Defining the nature of human γδ T cells: a biographical sketch of the highly empathetic, Cellular & Molecular Immunology* (2013) 10,21-29. γδ T cells can provide help to the CD8+ cells through release of cytokines, e.g., contributing to the activation, proliferation, and differentiation of CD8+ cells. Further, clinical significance of γδ T cells in the context of hematopoietic stem cell transplantation (HSCT) has been observed, and in particular, higher frequencies of γδ T cells after transplantation were associated with favorable outcomes. See Berglund et al., *Expansion of Gammadelta T cells from Cord Blood: A Therapeutic Possibility. Stem Cells International* Vol. 2018.

In various embodiments, the cell composition comprises at least about 2% γδ T cells, or at least about 5% γδ T cells. In some embodiments, the cell composition comprises at least about 10% γδ T cells, or at least about 20% γδ T cells. In some embodiments, the cell composition comprises at least about 25% γδ T cells, or at least about 30%, or at least about 35%, or at least about 40% γδ T cells, or at least about 45% γδ T cells. In these embodiments, the γδ T cells may comprise one or both of Vδ1 and Vδ2 cells. In some embodiments, a portion of the γδ T cells are CD8+. In various embodiments, the γδ T cells are predominately CD28+.

Cell compositions in accordance with various embodiments can be prepared by enrichment of CD8+ cells that are specific for the target antigen(s) (e.g., tumor associated antigens or viral-associated antigens). This cell population, even when predominately naive cells in the source lymphocytes, can be rapidly expanded in culture to arrive at the cell compositions described herein. CD4+ cells can be depleted (pre- or post- antigen-specific enrichment) from the lymphocytes using CD4+ cell depletion microbeads.

Antigen specific enrichment of CD8+ cells can take place using paramagnetic beads to positively select cell populations, and which can have the added advantage of activating naive cells due to potent magnetic clustering of T cell surface receptors. For example, paramagnetic beads or nanoparticles may contain monomeric or multimeric (e.g., dimeric) HLA ligands presenting peptide antigens, along with a co-stimulation signal in some embodiments, such as an agonist for CD28 (e.g., an antibody agonist of CD28). Exemplary methods according to these embodiments are described in WO 2016/044530, PCT/US2017/22663, and U.S. Pat. No. 10,908,939, which are hereby incorporated by reference in its entirety.

In some embodiments, CD28+ cells are also enriched, which can be simultaneous with antigen-specific enrichment. CD28 is expressed on T cells, and is a co-stimulatory signal required for T cell activation and survival. CD28 is the only B7 receptor constitutively expressed on naive T cells. Association of the TCR of a naive T cell with MHC-antigen complex without CD28 co-stimulation can result in a T cell that is anergic. In some embodiments, CD28+ cells are not enriched, but a CD28 agonist is added in soluble form during the enrichment process, or added as conjugated to non-paramagnetic beads. In some embodiments, CD28 (in conjugated or non-conjugated form) is added to the cells after antigen-specific enrichment, in order to activate cells for the expansion phase.

In various embodiments, the T cells specific for target antigens (e.g., by virtue of the peptides displayed by the aAPCs or pAPCs) are specific for from 1 to about 100 target antigens, or from 1 to about 75 target antigens, or from 1 to about 50 target antigens, or from 1 to about 25 target antigens, or from 1 to about 20 target antigens, or from 1 to about 15 target antigens, or from 1 to 10 target antigens, or from 1 to 5 target antigens. In various embodiments, there are at least 3, or at least 4, or at least 5 target antigens. The distinct target antigens can include overlapping peptide epitopes in some embodiments. T cells specific for these peptide antigens can be enriched and expanded in batch, allowing for rapid, parallel production of cell compositions. In some embodiments, the composition contains T cells specific for from 5 to 15 or from 5 to 10 peptide antigens. T cell specificity toward a target peptide antigen in the composition is defined by MHC multimer staining (e.g., dimer or tetramer staining) as is well known in the art.

For example, a cocktail of nano-aAPCs, each aAPC presenting a different, distinct target antigen, can be used to enrich T cells against multiple antigens simultaneously. For example, T cells specific for from 2 to 10 antigens can be enriched simultaneously from the lymphocyte source. In this embodiment, a number of different nano-aAPC batches, each bearing a different MHC-peptide, would be combined and used to simultaneously enrich T cells against each of the antigens of interest. The resulting T cell pool would be activated against each of these antigens, and expanded together in culture. These antigens could be related to a single therapeutic intervention; for example, multiple antigens present on a single tumor or malignant cell.

The target peptide antigens are generally suitable for presentation by an HLA-A, B, or C molecular complex, and in some embodiments an HLA-A2 molecular complex.

In various embodiments, the target peptide antigens are tumor or cancer associated antigens, including tumor-derived or tumor-specific antigens. T cells specific for tumor associated antigens are often very rare, and in many cases undetectable, in the peripheral blood of healthy individuals. Further, the cells are often of a naive phenotype, particularly when using donor T lymphocytes. See, Quintarelli et al., *Cytotoxic T lymphocytes directed to the preferentially expressed antigens of melanoma (PRAME) target chronic myeloid leukemia. Blood* 2008; 112: 1876-1885. This is often a distinction observed between viral-specific and tumor antigen specific T cells.

"Tumor-associated antigens" or "cancer specific antigens" include unique tumor or cancer antigens expressed exclusively by the tumor or malignant cells from which they are derived, shared tumor antigens expressed in many tumors but not in normal adult tissues (oncofetal antigens), and tissue-specific antigens expressed also by the normal tissue from which the tumor arose. Tumor associated antigens can be, for example, embryonic antigens, antigens with abnormal post-translational modifications, differentiation antigens, products of mutated oncogenes or tumor suppressors, fusion proteins, or oncoviral proteins.

In some embodiments, the target peptide antigens include one or more associated with or derived from hematological cancer, such as leukemia, lymphoma, or myeloma. For example, the hematological malignancy may be acute myeloid leukemia, chronic myelogenous leukemia, childhood acute leukemia, non-Hodgkin's lymphomas, acute lymphocytic leukemia, chronic lymphocytic leukemia, myelodysplastic syndrome, malignant cutaneous T-cells, mycosis fungoids, non-MF cutaneous T-cell lymphoma, lymphomatoid papulosis, and T-cell rich cutaneous lymphoid hyperplasia. In other embodiments, the target peptide antigens include one or more associated with or derived from a solid tumor, including melanoma, colon cancer, duodenal cancer, prostate cancer, breast cancer, ovarian cancer, ductal cancer, hepatic cancer, pancreatic cancer, renal cancer, endometrial cancer, testicular cancer, stomach cancer, dysplastic oral mucosa, polyposis, head and neck cancer, invasive oral cancer, non-small cell lung carcinoma, small-cell lung cancer, mesothelioma, transitional and squamous cell urinary carcinoma, brain cancer, neuroblastoma, and glioma.

A variety of tumor-associated antigens are known in the art. Oncofetal and embryonic antigens include carcinoembryonic antigen and alpha-fetoprotein (usually only highly expressed in developing embryos but frequently highly expressed by tumors of the liver and colon, respectively), MAGE-1 and MAGE-3 (expressed in melanoma, breast cancer, and glioma), placental alkaline phosphatase sialyl-Lewis X (expressed in adenocarcinoma), CA-125 and CA-19 (expressed in gastrointestinal, hepatic, and gynecological tumors), TAG-72 (expressed in colorectal tumors), epithelial glycoprotein 2 (expressed in many carcinomas), pancreatic oncofetal antigen, 5T4 (expressed in gastriccarcinoma), alphafetoprotein receptor (expressed in multiple tumor types, particularly mammary tumors), and M2A (expressed in germ cell neoplasia).

Tumor-associated differentiation antigens include tyrosinase (expressed in melanoma) and particular surface immunoglobulins (expressed in lymphomas).

Mutated oncogene or tumor-suppressor gene products include Ras and p53, both of which are expressed in many tumor types, Her-2/neu (expressed in breast and gynecological cancers), EGF-R, estrogen receptor, progesterone receptor, retinoblastoma gene product, myc (associated with lung cancer), ras, p53, nonmutant associated with breast tumors, MAGE-1, and MAGE-3 (associated with melanoma, lung, and other cancers). Fusion proteins include BCR-ABL, which is expressed in chromic myeloid leukemia. Oncoviral proteins include HPV type 16, E6, and E7, which are found in cervical carcinoma.

Tissue-specific antigens include melanotransferrin and MUC1 (expressed in pancreatic and breast cancers); CD10 (previously known as common acute lymphoblastic leukemia antigen, or CALLA) or surface immunoglobulin (expressed in B cell leukemias and lymphomas); the α chain of the IL-2 receptor, T cell receptor, CD45R, CD4+/CD8+ (expressed in T cell leukemias and lymphomas); prostate specific antigen and prostatic acid-phosphatase (expressed in prostate carcinoma); GP 100, MelanA/Mart-1, tyrosinase, gp75/brown, BAGE, and S-100 (expressed in melanoma); cytokeratins (expressed in various carcinomas); and CD19, CD20, and CD37 (expressed in lymphoma).

Tumor-associated antigens also include altered glycolipid and glycoprotein antigens, such as neuraminic acid-containing glycosphingolipids (e.g., GM2 and GD2, expressed in melanomas and some brain tumors); blood group antigens, particularly T and sialylated Tn antigens, which can be aberrantly expressed in carcinomas; and mucins, such as CA-125 and CA-19-9 (expressed on ovarian carcinomas) or the underglycosylated MUC-1 (expressed on breast and pancreatic carcinomas).

For example, in some embodiments, one or more target antigens are associated with bladder cancer, such as one or more of NY-ESO-1, MAGE-A10, and MUC-1 antigens. In some embodiments, one or more target antigens are associated with brain cancer, and may include one or more of NY-ESO-1, Survivin, and CMV antigens. In some embodiments, one or more target antigens are associated with breast cancer, and may include one or more of MUC-1, Surivin, WT-1, HER-2, and CEA antigens. In some embodiments, one or more target antigens are associated with cervical cancer, and may include HPV antigen. In some embodiments, one or more target antigens are associated with colorectal cancer, and may include one or more of NY-ESO-1, Survivin, WT-1, MUC-1, and CEA antigens. In some embodiments, one or more target antigens are associated with esophageal cancer, and may include NY-ESO-1 antigen. In some embodiments, one or more target antigens may be associated with head and neck cancer, and may include HPV antigen. In some embodiments, the target antigen is associated with kidney or liver cancer, and may include NY-ESO-1 antigen. In some embodiments, the target antigen is associated with lung cancer, and may include one or more of NY-ESO-1, Survivin, WT-1, MAGE-A10, and MUC-1 antigens. In some embodiments, one or more target antigens is associated with melanoma, and may include one or more of NY-ESO-1, Survivin, MAGE-A10, MART-1, and GP-100. In some embodiments, one or more peptide antigens are associated with ovarian cancer, and may include one or more of NY-ESO-1, WT-1, and Mesothelin antigen. In some embodiments, one or more target antigens are associated with prostate cancer, and may include one or more of Survivin, hTERT, PSA, PAP, and PSMA antigens. In some embodiments, the target antigen is associated with a sarcoma, and may include NY-ESO-1 antigen. In some embodiments, one or more target antigens are associated with lymphoma, and may include EBV antigen. In some embodiments, one or more target antigens are associated with multiple myeloma, and may include one or more of NY-ESO-1, WT-1, XBP1-US, XBP1-SP, CD138, CS1 (SLAMF7), and SOX2 antigens. In some embodiments, the target antigens associated with multiple myeloma are two or more of (or three, four, five, or six of) peptide antigens disclosed in U.S. Pat. No. 9,096,681, which is hereby incorporated by reference in its entirety. Exemplary peptides comprising antigenic epitopes include XBP1 unspliced $(UN)_{185-193}$, $XBP1-US_{184-192}$, XBP1 spliced $(SP)_{223-231}$, $XBP1-SP_{367-375}$, $CD138_{265-273}$, $CD138_{260-268}$, $CS1_{240-248}$, $CS1_{239-247}$, $NY-ESO1_{157-165A}$, and $SOX2_{118-127}$. In some embodiments, the target antigens comprise NY-ESO-1, WT-1, SOX-2, CD138, and CS1. In some embodiments, the target antigens comprise NY-ESO-1, WT-1, SOX-2, CD138, CS1, and XBP1-US and/or XBP1-SP. In some embodiments, the peptide antigens comprise NY-ESO-1, WT-1, and SOX-2. See Table 2.

In some embodiments, one or more target antigens are associated with acute myelogenous leukemia or myelodysplastic syndrome, and may include one or more of (including 1, 2, 3, 4, or 5 of) Survivin, WT-1, PRAME, RHAMM, PR3, and Cyclin A1 antigens. In some embodiments, the target antigens include at least 1, 2, 3, 4, 5, 6, 7, 8, 9, 10 or all target antigens from Table 1 below.

TABLE 1

Exemplary AML target peptide antigens

| Antigen | Peptide name/ position | Sequence | SEQ ID NO: |
|---|---|---|---|
| WT-1 | 126-134 | RMFPNAPYL | SEQ ID NO: 1 |
|  | 235-243 | CMTWNQMNL | SEQ ID NO: 2 |
|  | 37-45 | VLDFAPPGA | SEQ ID NO: 3 |
|  | 187-195 | SLGEQQYSV | SEQ ID NO: 4 |
| Prame | P100 | VLDGLDVLL | SEQ ID NO: 5 |
|  | P435 | NLTHVLYPV | SEQ ID NO: 6 |
|  | P142 | SLYSFPEPEA | SEQ ID NO: 7 |
|  | P300 | ALYVDSLFFL | SEQ ID NO: 8 |
|  | P425 | SLLQHLIGL | SEQ ID NO: 9 |
| Survivin | ELT 95-104 | ELTLGEFLKL | SEQ ID NO: 10 |
|  | LDR 104-113 | LDRERAKNKI | SEQ ID NO: 11 |
| Cyclin A1 | 227-235 | FLDRFLSCM | SEQ ID NO: 12 |
|  | 341-351 | SLIAAAFCLA | SEQ ID NO: 13 |

In some embodiments, one or more target antigens may include one or more of XBP1-US, XBP1-SP, CD138, CS1, NY-ESO1, SOX2, EBV, Influenza, CMV, RHAMM, PR3, Mart-1/Melan A, gp100, CMVpp65, and Influenza Matrix Protein M1 antigens. In some embodiments, the target antigens include at least 1, 2, 3, 4, 5, 6, 7, 8, 9, or 10 target antigens from Table 2 below, which are useful for targeting multiple myeloma, melanoma, or various viral or infectious diseases.

TABLE 2

Exemplary target peptide antigens

| Antigen | Peptide name/ position | Sequence | SEQ ID NO: | Restriction |
|---|---|---|---|---|
| XBP1-US | 184-192 | YISPWILAV | SEQ ID NO: 14 | — |
| XBP1-SP | 367-375 | YLFPQLISV | SEQ ID NO: 15 | — |
| CD138 | 260-268 | GLVGLIFAV | SEQ ID NO: 16 | — |
| CS1 | 239-247 | SLFVLGLFL | SEQ ID NO: 17 | — |
| NY-ESO1 | 157-165A | SLLMWITQA | SEQ ID NO: 18 | — |
| SOX2 | 118-127 | ALSPASSRSV | SEQ ID NO: 19 | — |
| LAMP2 | — | CLGGLLTMV | SEQ ID NO: 20 | A2 |
| LAMP2 | — | FLYALALLL | SEQ ID NO: 21 | A2 |
| BMLF1 | — | GLCTLVAML | SEQ ID NO: 22 | A2 |
| BRLF1 | — | YVLDHLIVV | SEQ ID NO: 23 | A2 |
| EBNA3 | — | LLDFVRFMGV | SEQ ID NO: 24 | A2 |
| LMP1 | — | YLQQNWWTL | SEQ ID NO: 25 | A2 |
| LMP2 | — | IYVLVMLVL | SEQ ID NO: 26 | A24 |
| BRLF1 | — | TYPVLEEMF | SEQ ID NO: 27 | A24 |
| BMLF1 | — | DYNFVKQLF | SEQ ID NO: 28 | A24 |
| EBNA3A | — | RYSIFFDYM | SEQ ID NO: 29 | A24 |
| EBNA3B | — | TYSAGIVQI | SEQ ID NO: 30 | A24 |
| EBNA-3A | — | RPPIFIRRL | SEQ ID NO: 31 | B7 |
| EBNA-3C | — | QPRAPIRPI | SEQ ID NO: 32 | B7 |
| BMRF1 | — | RPQGGSRPEFVKL | SEQ ID NO: 33 | B7 |
| M1 | — | GILGFVFTL | SEQ ID NO: 34 | A2 |
| PB1 | — | QPEWFRNVL | SEQ ID NO: 35 | B7 |
| NP | — | SPIVPSFDM | SEQ ID NO: 36 | B7 |
| pp65 | 341-349 | QYDPVAALF | SEQ ID NO: 37 | A24 |
| pp65 | 113-121 | VYALPLKML | SEQ ID NO: 38 | A24 |
| IE-1 | 248-256 | AYAQKIFKI | SEQ ID NO: 39 | A24 |
| pp65 | 417-426 | TPRVTGGGAM | SEQ ID NO: 40 | B7 |
| pp65 | 265-275 | RPHERNGFTVL | SEQ ID NO: 41 | B7 |
| RHAMM | R3 | ILSLELMKL | SEQ ID NO: 42 | — |
| RHAMM | R5 | SLEENIVIL | SEQ ID NO: 43 | — |
| RHAMM | R1 | KLLEYIEEI | SEQ ID NO: 44 | — |
| RHAMM | R2 | KLQEELNKV | SEQ ID NO: 45 | — |
| RHAMM | R8 | KLKGKEAEL | SEQ ID NO: 46 | — |
| PR3 | $PR-1_{169-177}$ | VLQELNVTV | SEQ ID NO: 47 | — |

TABLE 2-continued

Exemplary target peptide antigens

| Antigen | Peptide name/ position | Sequence | SEQ ID NO: | Restriction |
|---|---|---|---|---|
| Mart-1/Melan A | Mart-1 A27L | ELAGIGILTV | SEQ ID NO: 48 | — |
| gp100 | G209-2M gp100 (209-217) | IMDQVPFSV | SEQ ID NO: 49 | — |
| NY-ESO 1 | 157-165 | SLLMWITQC | SEQ ID NO: 50 | |
| NY-ESO 1 | 165A | SLLMWITQA | SEQ ID NO: 51 | — |
| CMVpp65 | pp65 | NLVPMVATV | SEQ ID NO 52 | — |
| XBP1-UN | 185-193 | ISPWILAVL | SEQ ID NO 53 | A24 |
| XBP1-SP | 223-231 | VYPEGSSL | SEQ ID NO 54 | A24 |
| CD138 | 265-273 | IFAVCLVGF | SEQ ID NO 55 | A24 |
| CS1 | 240-248 | LFVLGLFLW | SEQ ID NO 56 | A24 |

In some embodiments, one or more target peptide antigens are neoantigens. For example, in some embodiments, neoantigens specific to the patient are identified, and synthesized for loading aAPCs. In some embodiments, between three and ten neoantigens are identified through genetic analysis of the patient's malignancy (e.g., by nucleic acid sequencing of malignant cells), followed by predictive bioinformatics. In some embodiments, the antigens are natural, non-mutated, cancer antigens, of which many are known.

In various embodiments, at least one of the target peptide antigens is recognized by a low frequency precursor T cell. In accordance with these embodiments, the invention enables rapid activation and expansion of these cells for adoptive therapy.

In some embodiments, the target peptide antigens include at least one that is associated with or derived from a pathogen, such as a viral, bacterial, fungal, or parasitic pathogen. For example, at least one peptide antigen may be associated with HIV, hepatitis (e.g., A, B, C, or D) CMV, Epstein-Barr virus (EBV), influenza, herpes virus (e.g., HSV 1 or 2, or varicella zoster), and Adenovirus. CMV, for example, is the most common viral pathogen found in organ transplant patients and is a major cause of morbidity and mortality in patients undergoing bone marrow or peripheral blood stem cell transplants. This is due to the immunocompromised status of these patients, which permits reactivation of latent virus in seropositive patients or opportunistic infection in seronegative individuals. In these embodiments, the patient may receive adoptive immunotherapy comprising T cells specific for pathogen antigens. The method can entail generation of virus-specific CTL derived from the patient or from an appropriate donor before initiation of the transplant procedure.

In some embodiments, at least one target antigen is a pathogen-associated antigen, including antigens associated with protozoa, bacteria, fungi (both unicellular and multicellular), viruses, prions, intracellular parasites, helminths, and other infectious agents.

Bacterial antigens include antigens of gram-positive cocci, gram positive bacilli, gram-negative bacteria, anaerobic bacteria, such as organisms of the families Actinomycetaceae, Bacillaceae, Bartonellaceae, Bordetellae, Captophagaceae, Corynebacteriaceae, Enterobacteriaceae, Legionellaceae, Micrococcaceae, Mycobacteriaceae, Nocardiaceae, Pasteurellaceae, Pseudomonadaceae, Spirochaetaceae, Vibrionaceae and organisms of the genera *Acinetobacter, Brucella, Campylobacter, Erysipelothrix, Ewingella, Francisella, Gardnerella, Helicobacter, Levinea, Listeria, Streptobacillus* and *Tropheryma*.

Antigens of protozoan infectious agents include antigens of malarial plasmodia, *Leishmania* species, *Trypanosoma* species and *Schistosoma* species.

Fungal antigens include antigens of Aspergillus, Blastomyces, Candida, Coccidioides, Cryptococcus, Histoplasma, Paracoccicioides, Sporothrix, organisms of the order Mucorales, organisms inducing choromycosis and mycetoma and organisms of the genera *Trichophyton, Microsporum, Epidermophyton,* and *Malassezia*.

Viral peptide antigens include, but are not limited to, those of adenovirus, herpes simplex virus, papilloma virus, respiratory syncytial virus, poxviruses, HIV, influenza viruses, EBV, hepatitis, and CMV. Particularly useful viral peptide antigens include HIV proteins such as HIV gag proteins (including, but not limited to, membrane anchoring (MA) protein, core capsid (CA) protein and nucleocapsid (NC) protein), HIV polymerase, influenza virus matrix (M1) protein and influenza virus nucleocapsid (NP) protein, hepatitis B surface antigen (HBsAg), hepatitis B core protein (HBcAg), hepatitis e protein (HBeAg), hepatitis B DNA polymerase, hepatitis C antigens, and the like.

In some embodiments, the target peptide antigens include one or more tumor associated antigens, and one or more virus-associated antigens (such as CMV, EBV, influenza, or Adenovirus), to provide an antitumor response while protecting against common pathogens that complicate recovery after HSCT.

Patients that have undergone HSCT are at particular risk for infectious disease, given the immunocompromised state. The immunocompromised status of these patients permits reactivation of latent virus in seropositive patients or opportunistic infection in seronegative individuals. For example, post-transplant lymphoproliferative disease (PTLD) occurs in a significant fraction of transplant patients and results from Epstein-Barr virus (EBV) infection. EBV infection is believed to be present in approximately 90% of the adult population in the United States. Active viral replication and infection is kept in check by the immune system, but, as in cases of CMV, individuals immunocompromised by transplantation therapies lose the controlling T cell populations, which permits viral reactivation. This represents a serious impediment to transplant protocols. EBV may also be involved in tumor promotion in a variety of hematological and non-hematological cancers.

In still other embodiments, the cell composition comprises T cells specific for tumor associated antigens, with pathogen-associated T cells provided as bystander cells. Specifically, by enriching for CD8+ T cells based on selection with both HLA-peptide complexes and anti-CD28, bystander cells will be enriched, and expanded, particularly when using a T cell growth factor cocktail that can drive some non-specific expansion of these cells without antigen-specific activation. In these embodiments, while a large portion of the composition are T cells specific for the target peptides (e.g., from 5% to 75%, or from 10 to 50%), the remaining T cells provide some reconstitution of the immune system against common pathogens, which is particularly beneficial after transplant. For example, the composition may comprise T cells specific for CMV, EBV, influenza, and Adenovirus. In each case, pathogen-specific T cells may be present at from 0.1% to about 4% of the composition.

In various embodiments the invention involves compositions prepared by enrichment and expansion of antigen-specific CD8+ T cells. Precursor T cells can be obtained from the patient or from a suitable HLA-matched donor. Source T cells can be either fresh or frozen samples. Precursor T cells can be obtained from a number of sources that comprise WBCs, including peripheral blood mononuclear cells (PBMC), bone marrow, lymph node tissue, spleen tissue, buffy coat fraction, and tumors. In some embodiments, precursor T cells are obtained from a unit of blood collected from a subject using any number of techniques known to one or skill in the art. For example, precursor T cells from the circulating blood of an individual can be obtained by apheresis or leukapheresis. The apheresis product typically contains lymphocytes, including T cells and precursor T cells, monocytes, granulocytes, B cells, other nucleated white blood cells, red blood cells, and platelets. Leukapheresis is a laboratory procedure in which white blood cells are separated from a sample of blood.

Cells collected by apheresis can be washed to remove the plasma fraction and to place the cells in an appropriate buffer or media for subsequent processing steps. Washing steps can be accomplished by methods known to those in the art, such as by using a semi-automated "flow-through" centrifuge. After washing, the cells may be resuspended in a variety of biocompatible buffers, such as, for example, Ca-free, Mg-free PBS. Alternatively, the undesirable components of the apheresis sample can be removed and the cells directly re-suspended in a culture medium.

If desired, precursor T cells can be isolated from peripheral blood lymphocytes by lysing the red blood cells and depleting the monocytes, for example, by centrifugation through a PERCOLL™ gradient.

In certain embodiments, leukocytes are collected by leukapheresis, and may be subsequently enriched for CD8+ T cells, for example, by depleting the sample of CD4+ cells and/or positively enriching for CD8+ cells. In some embodiments, other cell types are depleted, such as NK cells. The CD8-enriched cells may then be further enriched for antigen-specific T cells.

In various embodiments, the sample comprising the immune cells (e.g., CD8+ T cells) is contacted with an artificial Antigen Presenting Cell (aAPC) having magnetic properties. Paramagnetic materials have a small, positive susceptibility to magnetic fields. These materials are attracted by a magnetic field and the material does not retain the magnetic properties when the external field is removed. Exemplary paramagnetic materials include, without limitation, magnesium, molybdenum, lithium, tantalum, and iron oxide. Paramagnetic beads suitable for magnetic enrichment are commercially available (DYNABEADS™, MACS MICROBEAD™, Miltenyi Biotec). In some embodiments, the aAPC particle is an iron dextran bead (e.g., dextran-coated iron-oxide bead).

Antigen presenting complexes comprise an antigen binding cleft, and are generally MHC class I, which can be linked or tethered to provide dimeric or multimeric MHC. In some embodiments, the MHC are monomeric, but their close association on the nano-particle is sufficient for avidity and activation. In some embodiments, the MHC are dimeric. Dimeric MHC class I ligands can be constructed by fusion to immunoglobulin heavy chain sequences, which are then associated through one or more disulfide bonds (with or without associated light chains). MHC multimers can be created by direct tethering through peptide or chemical linkers, or can be multimeric via association with streptavidin through biotin moieties. In some embodiments, the antigen presenting complexes are MHC class I complexes involving fusions with immunoglobulin sequences.

MHC class I molecular complexes having immunoglobulin sequences are described in U.S. Pat. No. 6,268,411, which is hereby incorporated by reference in its entirety. These MHC class I molecular complexes may be formed in a conformationally intact fashion at the ends of immunoglobulin heavy chains. MHC class I molecular complexes to which antigenic peptides are bound can stably bind to antigen-specific lymphocyte receptors (e.g., T cell receptors). In various embodiments, the immunoglobulin heavy chain sequence is not full length, but comprises an Ig hinge region, and one or more of CH1, CH2, and/or CH3 domains. The Ig sequence may or may not comprise a variable region, but where variable region sequences are present, the variable region may be full or partial. The complex may further comprise immunoglobulin light chains. MHC class I ligands (e.g., HLA-Ig) lacking variable chain sequences (and lacking any light chain) may be employed with site-directed conjugation to particles, as described in WO 2016/105542, which is hereby incorporated by reference in its entirety.

Exemplary MHC class I molecular complexes comprise at least two fusion proteins. A first fusion protein comprises a first MHC class I α chain and a first immunoglobulin heavy chain (or portion thereof comprising the hinge region), and a second fusion protein comprises a second MHC class I α chain and a second immunoglobulin heavy chain (or portion thereof comprising the hinge region). The first and second immunoglobulin heavy chains associate to form the MEW class I molecular complex, which comprises two MHC class I peptide-binding clefts. The immunoglobulin heavy chain can be the heavy chain of an IgM, IgD, IgG1, IgG3, IgG2β, IgG2α, IgG4, IgE, or IgA. In some embodiments, an IgG heavy chain is used to form MEW class I molecular complexes. If multivalent MHC class I molecular complexes are desired, IgM or IgA heavy chains can be used to provide pentavalent or tetravalent molecules, respectively.

Exemplary class I molecules include HLA-A, HLA-B, HLA-C, HLA-E, and these may be employed individually or in any combination. In some embodiments, the antigen presenting complex is an HLA-A2 ligand. The term MHC as used herein, can be replaced by HLA in each instance.

Immunoglobulin sequences in some embodiments are humanized monoclonal antibody sequences.

The aAPCs may contain a "Signal 2", such as an anti-CD28 ligand. Signal 2 is generally a T cell affecting molecule, that is, a molecule that has a biological effect on a precursor T cell or on an antigen-specific T cell. In certain embodiments, signal 2 is a T cell costimulatory molecule. T cell costimulatory molecules contribute to the activation of antigen-specific T cells. Such molecules include, but are not limited to, molecules that specifically bind to CD28 (including antibodies), CD80 (B7-1), CD86 (B7-2), B7-H3, 4-1BB, 4-1BBL, CD27, CD30, CD134 (OX-40L), B7h (B7RP-1), CD40, LIGHT, antibodies that specifically bind to HVEM, antibodies that specifically bind to CD40L, and antibodies that specifically bind to OX40. In some embodiments, the costimulatory molecule (signal 2) is an antibody (e.g., a monoclonal antibody) or portion thereof, such as F(ab')2, Fab, scFv, or single chain antibody, or other antigen binding fragment. In some embodiments, the antibody is a humanized monoclonal antibody or portion thereof having antigen-binding activity, or is a fully human antibody or portion thereof having antigen-binding activity.

Combinations of co-stimulatory ligands that may be employed (on the same or separate nanoparticles) include anti-CD28/anti-CD27 and anti-CD28/anti-41BB. The ratios of these co-stimulatory ligands can be varied to effect expansion.

Exemplary signal 1 and signal 2 ligands are described in WO 2014/209868, which describe ligands having a free sulfhydryl (e.g., unpaired cysteine), such that the constant region may be coupled to nanoparticle supports having the appropriate chemical functionality.

Adhesion molecules useful for nano-aAPC can be used to mediate adhesion of the nano-aAPC to a T cell or to a T cell precursor. Useful adhesion molecules include, for example, ICAM-1 and LFA-3.

In some embodiments, signal 1 is provided by peptide-HLA-A2 complexes, and signal 2 is provided by B7.1-Ig or anti-CD28. An exemplary anti-CD28 monoclonal antibody is 9.3 mAb (Tan et al., J. Exp. Med. 1993 177:165), which may be humanized in certain embodiments and/or conjugated to the bead as a fully intact antibody or an antigen-binding fragment thereof.

Magnetic activation may take place for from 2 minutes to 5 hours, or from 5 minutes to 2 hours, followed by expansion in culture for at least 5 days, and up to 2 weeks or up to 3 weeks in some embodiments. In some embodiments, magnetic activation occurs for at least 2 minutes, but less than 30 minutes or less than 15 minutes (e.g., about 5 or 10 minutes). Resulting CD8+ T cells may be phenotypically characterized to confirm the presence of T memory stem cells ($T_{scm}$), as well as high central and effector memory phenotype.

Some embodiments employ T cell growth factors during expansion, which affect proliferation and/or differentiation of T cells. Examples of T cell growth factors include cytokines (e.g., interleukins, interferons) and superantigens. If desired, cytokines can be present in molecular complexes comprising fusion proteins, or can be encapsulated by the aAPC, or provided in soluble form. Particularly useful cytokines include MIP-1β, IL-1β, IL-2, IL-4, IL-6, IL-7, IL-10, IL-12, IL-15, IL-21, IFN-γ, and CXCL10. In some embodiments, the growth factors include 3, 4, 5, or 6 from MIP-1β, IL-1β, IL-2, IL-4, IL-6, IL-7, IL-10, IL-15, IL-21, and INF-γ. In these or other embodiments, the cells are expanded in culture in the presence cytokines including one, two, three cytokines selected from MIP-1β, IL-1β, IL-6, and IL-10. In some embodiments, the cells are not cultured in the presence of IL-7 and/or IL-21 and/or IL-15. Cells can be expanded in culture from 1 to 4 weeks, such as about 2 weeks (about 14 days), or about 3 weeks.

In some embodiments, the cells are expanded in culture in the presence of from 4 to 8 cytokines, to achieve a balance between T cell expansion (including antigen-specific T cell expansion), activation, and memory phenotype. In some embodiments, the cells are expanded in the presence of IL-4. In some embodiments, the cells are expanded in the presence of IL-4 and IL-6. In some embodiments, the cells are expanded in the presence of IL-4 and IL-1β. In some embodiments, the cells are expanded in the presence of IL-4, IL-6, and IL-1β. In some embodiments, the cells are expanded in the presence of IL-2, IL-4, and IL-6. In some embodiments, the cells are expanded in culture in the presence of IL-2, IL-4, IL-6, INF-γ, and IL-1β. In some embodiments, the cells are further expanded in the presence of IL-10. In various embodiments, these cytokines are used in conjunction with artificial or natural antigen presenting cells to expand antigen specific T cells.

In some embodiments, the growth factors consist, or consist essentially of, IL-2, IL-4, IL-6, INF-γ, IL-1β, and optionally IL-10.

In some embodiments, IL-2 is present at the start of culture at 10 to 200 International Units (IU) per ml, such as from about 20 to about 100 IU/ml, or about 20 to about 60 IU/ml. In some embodiments, IL-2 is present at the start of culture at about 30 to about 50 IU/ml (e.g., about 40 IU/ml). IL-2 IU (86/500 NIBSC) can be determined using a proliferation assay (e.g., using CTLL-2 cell line), as described for example by Gearing and Bird (1987) in *Lymphokines and Interferons, A Practical Approach*. Clemens, M J et al. (eds): IRL Press. 295. In some embodiments, IL-2 is present at the start of culture at about 2 to about 25 ng/ml, or at about 2 to about 15 ng/ml, such as from about 5 to about 15 ng/ml.

In these or independent embodiments, IL-4 is present at the start of culture at 0.2 to 25 International Units (IU) per ml, such as from about 0.5 to about 10 IU/ml, or from about 0.5 to about 5 IU/ml. In some embodiments, IL-4 is present at the start of culture at about 1 IU/ml. IL-4 IU (88/656 NIBSC) can be defined using a proliferation assay (e.g., using TF-1 cell line), as described for example, by Kitamura T. et al., (1991) *IL-1 up-regulates the expression of cytokine receptors on a factor-dependent human hemopoietic cell line, TF-1*. Int. Immunol. 3:571-577. In some embodiments, IL-4 is present at the start of culture at about 0.2 to about 2 ng/ml, such as from about 0.2 to about 1 ng/ml (e.g., about 0.5 ng/ml).

In these or independent embodiments, IL-6 may be present at the start of culture at 10 to 200 International Units (IU) per ml, such as from about 25 to about 100 IU/ml, such as from 25 to 75 IU/ml. In some embodiments, IL-6 is present at the start of culture at about 40 to about 60 IU/ml (e.g., about 50 IU/ml). IL-6 IU (89/548 NIBSC) can be defined using a proliferation assay (e.g., using B9 cell line), as described for example by Gaines-Das R E and Poole S. (1993) *The international standard for interleukin-6. Evaluation in an international collaborative study. J. Immunol. Methods* 160:147-153. In some embodiments, IL-6 is present at the start of culture at about 0.2 to about 10 ng/ml, such as from about 0.2 to about 5 ng/ml (e.g., about 0.2 to 1 ng/ml, or about 0.5 to 2 ng/ml).

In these or independent embodiments, Interferon gamma (INF-γ) may be present at the start of culture at from 10 to 200 International Units (IU) per ml, such as from about 20 to about 100 IU/ml, or from 20 to 60 IU/ml. In some embodiments, INF-γ is present at the start of culture at about 30 to about 50 IU/ml (e.g., about 40 IU/ml). INF-γ IU (87/586 NIBSC) can be defined using an antiviral assay (e.g., with Hela cells infected with EMC), as described for example in Meager A. (1987) *in Lymphokines and interferons, a Practical Approach*. Clemens, M J, et al. (eds): IRL Press. 129. In some embodiments, INF-γ is present at the start of culture at about 0.5 to about 20 ng/ml, such as from about 0.5 to about 10 ng/ml, or from about 0.5 to about 5 ng/ml, or from about 1 to about 10 ng/ml (e.g., from 1 to 5 ng/ml).

IL-1β may be present at the start of culture at 5 to 100 International Units (IU) per ml, such as from about 10 to about 50 IU/ml, such as from about 10 to about 30 IU/ml. In some embodiments, IL-1β is present at the start of culture at about 10 to about 20 IU/ml (e.g., about 15 IU/ml). IL-1β IU (86/680 NIBSC) can be defined using a proliferation assay (e.g., using D.10.G4.1 cells), as described for example by Poole, S. and Gaines-Das, R E (1991) *The international standards for interleukin-1 alpha and interleukin-1 beta. Evaluation in an international collaborative study. J. Immu-*

*nol. Methods* 142:1-13. In some embodiments, IL-1β is present at the start of culture at about 0.1 to 5 ng/ml, or at about 0.2 to about 5 ng/ml, such as from about 0.2 to about 2 ng/ml, or from about 0.2 to about 1 ng/ml.

In various embodiments, the cells are cultured in the presence of a growth factor cocktail comprising or consisting of IL-2, IL-4, IL-6, INF-γ, and IL-1β. In some embodiments, the relative activity (defined by the respective IU) of IL-2 and INF-γ is about 0.5:1 to about 1:0.5 (e.g., about 1:1). In these or independent embodiments, the relative activity (defined by respective IU) of IL-2 and IL-6 is about 0.5:1 to 1:0.5. In these or independent embodiments, the relative activity of IL-1β with respect to IL-2, IL-6, and/or IFN-γ (defined by respective IUs) is from 1:4 to 1:2 (e.g., about 1:3). In these or independent embodiments, the relative activity of IL-4 with respect to IL-2, IL-6, and/or IFN-γ (defined by respective IUs) is from 1:30 to 1:60. In these or independent embodiments, the relative activity of IL-4 with respect to IL-1β (defined by respective IUs) is from about 1:5 to about 1:25, such as from about 1:10 to about 1:20.

In some embodiments, the specific activity of each growth factor (IL-2, IL-4, IL-6, INF-γ, and IL-1β) at the start of culture (in IUs) can be shown as a percentage when the total IUs of all the growth factors in the culture is considered as 100%. For example, in some embodiments, the percentage of each growth factor in the culture can be as follows:

20% to 40% *IL-2* (e.g., 20 to 30% *IL-2*);

0.5% to 5% *IL-4* (e.g., 1 to 3% *IL-4*);

25% to 50% *IL-6* (e.g., 30 to 40% *IL-6*);

20% to 40% *IFN-γ* (e.g., 20 to 30% *IFN-γ*); and

5% to 20% *IL-1β* (e.g., 5 to 15% *IL-1β*).

The aAPC nanoparticles can be made of any material, and materials can be appropriately selected for the desired magnetic property, and may comprise, for example, metals such as iron, nickel, cobalt, or alloy of rare earth metal. Paramagnetic materials also include magnesium, molybdenum, lithium, tantalum, and iron oxide. Paramagnetic beads suitable for enrichment of materials (including cells) are commercially available, and include iron dextran beads, such as dextran-coated iron oxide beads. In aspects of the invention where magnetic properties are not required, nanoparticles can also be made of nonmetal or organic (e.g., polymeric) materials such as cellulose, ceramics, glass, nylon, polystyrene, rubber, plastic, or latex. In exemplary material for preparation of nanoparticles is poly(lactic-co-glycolic acid) (PLGA) or PLA and copolymers thereof, which may be employed in connection with these embodiments. Other materials including polymers and co-polymers that may be employed include those described in PCT/US2014/25889, which is hereby incorporated by reference in its entirety.

In various embodiments, the particle has a size (e.g., average diameter) within about 10 to about 500 nm, or within about 40 to about 400 nm, or within about 40 nm to 200 nm. For magnetic clustering, it is preferred that the nanoparticles have a size (mean diameter) in the range of 10 to 250 nm, or 50 to 200 nm, or 80 to 200 nm, or 20 to 100 nm in some embodiments. Receptor-ligand interactions at the cell-nanoparticle interface are not well understood. However, nanoparticle binding and cellular activation are sensitive to membrane spatial organization, which is particularly important during T cell activation, and magnetic fields can be used to manipulate cluster-bound nanoparticles to enhance activation. For example, T cell activation induces a state of persistently enhanced nanoscale TCR clustering and nanoparticles are sensitive to this clustering in a way that larger particles are not.

Furthermore, nanoparticle interactions with TCR clusters can be exploited to enhance receptor triggering. T cell activation is mediated by aggregation of signaling proteins, with "signaling clusters" hundreds of nanometers across, initially forming at the periphery of the T cell-APC contact site and migrating inward. As described herein, an external magnetic field can be used to enrich antigen-specific T cells (including rare naive cells) and to drive aggregation of magnetic nano-aAPC bound to TCR, resulting in aggregation of TCR clusters and enhanced activation of naive T cells. Magnetic fields can exert appropriately strong forces on paramagnetic particles, but are otherwise biologically inert, making them a powerful tool to control particle behavior. T cells bound to paramagnetic nano-aAPC are activated in the presence of an externally applied magnetic field. Nano-aAPC are themselves magnetized, and attracted to both the field source and to nearby nanoparticles in the field, inducing bead and thus TCR aggregation to boost aAPC-mediated activation.

Activation chemistries can be used to allow the specific, stable attachment of molecules to the surface of nanoparticles. There are numerous methods that can be used to attach proteins to functional groups. For example, the common cross-linker glutaraldehyde can be used to attach protein amine groups to an aminated nanoparticle surface in a two-step process. The resultant linkage is hydrolytically stable. Other methods include use of cross-linkers containing n-hydrosuccinimido (NHS) esters which react with amines on proteins, cross-linkers containing active halogens that react with amine-, sulfhydryl-, or histidine-containing proteins, cross-linkers containing epoxides that react with amines or sulfhydryl groups, conjugation between maleimide groups and sulfhydryl groups, and the formation of protein aldehyde groups by periodate oxidation of pendant sugar moieties followed by reductive amination.

The ratio of particular ligands when used simultaneously on the same or different particles can be varied to increase the effectiveness of the nanoparticle in antigen or costimulatory ligand presentation. For example, nanoparticles can be coupled with HLA-A2-Ig and anti-CD28 (or other signal 2 ligands) at a variety of ratios, such as about 30:1, about 25:1, about 20:1, about 15:1, about 10:1, about 5:1, about 3:1, about 2:1, about 1:1, about 0.5:1, about 0.3:1; about 0.2:1, about 0.1:1, or about 0.03:1. In some embodiments, the ratio is from 2:1 to 1:2. The total amount of protein coupled to the supports may be, for example, about 250 mg/ml, about 200 mg/ml, about 150 mg/ml, about 100 mg/ml, or about 50 mg/ml of particles. Because effector functions such as cytokine release and growth may have differing requirements for Signal 1 versus Signal 2 than T cell activation and differentiation, these functions can be determined separately.

In certain embodiments, the aAPCs are paramagnetic particles in the range of 50 to 150 nm, with a PDI (size distribution) of less than 0.2, or in some embodiments less than 0.1. The aAPCs may have a surface charge of from 0 to −10 mV, such as from about −2 to −6 mV. aAPCs may have from 10 to 120 ligands per particle, such as from about 25 to about 100 ligands per particle, with ligands conjugated to the particle through a free cysteine introduced in the Fc region of the immunoglobulin sequences. The particles may contain about 1:1 ratio of HLA dimer:anti-CD28, which may be present on the same or different populations of particles.

The nanoparticles provide potent expansion of cognate T cells, while exhibiting no stimulation of non-cognate TCRs, even with passive loading of peptide antigen. Particles are stable in lyophilized form for at least two or three years.

After enrichment and expansion, the antigen-specific T cell component of the sample will be at least about 5%, or at least about 10%, or at least about 15%, or at least about 20%, or at least about 25% antigen specific T cells. Further, these T cells comprise T memory stem cells, and can also comprise central and effector memory T cells. From the original sample isolated from the patient or donor, the antigen-specific T cells in various embodiments are expanded (in about 7 days) from about 100-fold to about 10,000 fold, such as at least about 100-fold, or at least about 200-fold. After 2 weeks, antigen-specific T cells are expanded at least 1000-fold, or at least about 2000-fold, at least about 3,000 fold, at least about 4,000-fold, or at least about 5,000-fold in various embodiments. In some embodiments, antigen-specific T cells are expanded by greater than 5000-fold or greater than 10,000 fold after two weeks. After one or two weeks of expansion, at least about $10^6$, or at least about $10^7$, or at least about $10^8$, or at least about $10^9$ antigen-specific T cells are obtained.

Suitable incubation conditions (culture medium, temperature, etc.) include those used to culture T cells or T cell precursors, as well as those known in the art for inducing formation of antigen-specific T cells using DC or artificial antigen presenting cells.

The cell composition can be administered to patients by any appropriate routes, including intravenous infusion, intra-arterial administration, intralymphatic administration, and intratumoral administration.

In some embodiments, the patient receives or initiates immunotherapy with one or more checkpoint inhibitors, prior to (or optionally after) receiving the cell composition by adoptive transfer. In various embodiments, the checkpoint inhibitor(s) target one or more of CTLA-4 or PD-1/PD-L1, which may include antibodies against such targets, such as monoclonal antibodies, or portions thereof, or humanized or fully human versions thereof. In some embodiments, the checkpoint inhibitor therapy comprises ipilimumab or Keytruda (pembrolizumab), or comparable monoclonal antibody. In some embodiments, the patient previously received PD1 blockade therapy, and was refractory or only partially responsive to that treatment. In such embodiments, the cell composition described herein can restore a robust T cell response, optionally in combination with a second round of immunotherapy (e.g., anti-CTLA4 or PD-1 blockade therapy).

In some embodiments, the patient receives about 1 to 5 rounds of adoptive immunotherapy (e.g., one, two, three, four or five rounds). In some embodiments, each administration of adoptive immunotherapy is conducted simultaneously with, or after (e.g., from about 1 day to about 1 week after), a round of checkpoint inhibitor therapy. In some embodiments, adoptive immunotherapy is provided about 1 day, about 2 days, about 3 days, about 4 days, about 5 days, about 6 days, or about 1 week after a checkpoint inhibitor dose. In some embodiments, the patient receives only a single administration of the cell composition.

In some aspects, the invention provides methods for personalized cancer immunotherapy. The methods are accomplished using the aAPCs to identify antigens to which the patient will respond, followed by administration of the appropriate peptide-loaded aAPC to the patient, or followed by enrichment and expansion of the antigen specific T cells ex vivo.

Genome-wide sequencing has dramatically altered our understanding of cancer biology. Sequencing of cancers has yielded important data regarding the molecular processes involved in the development of many human cancers. Driving mutations have been identified in key genes involved in pathways regulating three main cellular processes (1) cell fate, (2) cell survival and (3) genome maintenance. Vogelstein et al., Science 339, 1546-58 (2013).

Genome-wide sequencing also has the potential to revolutionize our approach to cancer immunotherapy. Sequencing data can provide information about both shared as well as personalized targets for cancer immunotherapy. In principle, mutant proteins are foreign to the immune system and are putative tumor-specific antigens. Indeed, sequencing efforts have defined hundred if not thousands of potentially relevant immune targets. Limited studies have shown that T cell responses against these neo-epitopes can be found in cancer patients or induced by cancer vaccines. However, the frequency of such responses against a particular cancer and the extent to which such responses are shared between patients are not well known. One of the main reasons for our limited understanding of tumor-specific immune responses is that current approaches for validating potential immunologically relevant targets are cumbersome and time consuming.

Although central tolerance abrogates T cell responses against self-proteins, oncogenic mutations induce neo-epitopes against which T cell responses can form. Mutation catalogues derived from whole exome sequencing provide a starting point for identifying such neo-epitopes. Using HLA binding prediction algorithms (Srivastava, PLoS One 4, e6094 (2009), it has been predicted that each cancer can have up 7-10 neo-epitopes. A similar approach estimated hundreds of tumor neo-epitopes. Such algorithms, however, may have low accuracy in predicting T cell responses, and only 10% of predicted HLA-binding epitopes are expected to bind in the context of HLA (Lundegaard C, Immunology 130, 309-18 (2010)). Thus, predicted epitopes must be validated for the existence of T cell responses against those potential neo-epitopes.

In certain embodiments, the nano-aAPC system is used to screen for neo-epitopes that induce a T cell response in a variety of cancers, or in a particular patient's cancer. Cancers may be genetically analyzed, for example, by whole exome-sequencing.

A list of candidate peptides can be generated from overlapping nine amino acid windows in mutated proteins. All nine-AA windows that contain a mutated amino acid, and 2 non-mutated "controls" from each protein will be selected. These candidate peptides will be assessed computationally for MHC binding using a consensus of MHC binding prediction algorithms, including Net MHC and stabilized matrix method (SMM). Nano-aAPC and MHC binding algorithms have been developed primarily for HLA-A2 allele. The sensitivity cut-off of the consensus prediction can be adjusted until a tractable number of mutation containing peptides (~500) and non-mutated control peptides (~50) are identified.

In an exemplary embodiment, the cell composition comprises, in a pharmaceutically acceptable carrier: at least 70%, at least 80% or at least 90% CD8+ or CD4− T cells and less than 5% CD4+ T cells; and at least 5% $T_{SCM}$ cells, where the CD8+ cells comprise at least $10^6$ T cells specific for from 1 to 10 target peptide antigens. Optionally, the CD8+ or CD4− T cells may comprise T cells specific for bacterial, viral, fungal and/or parasitic pathogens. In various embodiments, at least 30% of the CD8+ or CD4− T cells are $T_{SCM}$, central, and effector memory T cells, with less than 10% of the CD8+ or CD4− T cells being terminally differentiated T cells and less than 10% of the CD8+ or CD4− cells being naive cells. In various embodiments, at least 50% of the CD8+ or CD4− T cells specific for the target peptide antigens are $T_{SCM}$, central and effector memory T cells. In some embodiments, the cell composition comprises from about 5% at about 25% T memory stem cells ($T_{scm}$), or from about 5% to about 20% T memory stem cells.

In various embodiments, the cell composition further comprises γδ T cells. For example, the cell composition may comprise at least about 2% γδ T cells, or at least about 5% γδ T cells. In some embodiments, the cell composition comprises at least about 10% γδ T cells, or at least about 20% γδ T cells. In some embodiments, the cell composition comprises at least about 25% γδ T cells, or at least about 30%, or at least about 35%, or at least about 40% γδ T cells. In these embodiments, the γδ T cells may comprise one or both of Vδ1 and Vδ2 cells. In some embodiments, the γδ T cells are predominantly Vδ2 (e.g., at least about 60% or at least about 75%). In some embodiments, a portion of the γδ T cells are CD8+. In various embodiments, the γδ T cells are predominately CD28+.

In some embodiments, the cell composition further comprises a pharmaceutically acceptable carrier suitable for intravenous infusion, and which may be suitable as a cryoprotectant. An exemplary carrier is DMSO (e.g., about 10%). Cell compositions may be provided in unit vials or bags, and stored frozen until use. Unit doses may comprise from about $5 \times 10^5$ to about $5 \times 10^6$ cells per ml, in a volume of from 50 to 200 ml. In certain embodiments, the volume of the composition is ≤100 ml (e.g., from 50 to 100 ml).

In some aspects, the invention provides a method for treating a patient with cancer, comprising administering the cell composition described herein to a patient in need.

In some embodiments, the patient has a hematological cancer, which in some embodiments has relapsed after allogeneic stem cell transplantation. In some embodiments, the patient has acute myelogenous leukemia (AML) or myelodysplastic syndrome.

Other cancers that can be treated according to this disclosure include cancers that historically illicit poor immune responses or have a high rate of recurrence. Exemplary cancers include various types of solid tumors, including carcinomas, sarcomas, and lymphomas. In various embodiments the cancer is melanoma (including metastatic melanoma), colon cancer, duodenal cancer, prostate cancer, breast cancer, ovarian cancer, ductal cancer, hepatic cancer, pancreatic cancer, renal cancer, endometrial cancer, testicular cancer, stomach cancer, dysplastic oral mucosa, polyposis, head and neck cancer, invasive oral cancer, non-small cell lung carcinoma, small-cell lung cancer, mesothelioma, transitional and squamous cell urinary carcinoma, brain cancer, neuroblastoma, and glioma. In various embodiments, the cancer is stage I, stage II, stage III, or stage IV. In some embodiments, the cancer is metastatic and/or recurrent, and/or is nonresectable.

In some embodiments, the patient is refractory to chemotherapy and/or checkpoint inhibitor therapy.

In some embodiments, the patient further receives low dose cytokine therapy, which may improve the persistence and in vivo response.

In some embodiments, the cancer is a hematological malignancy, including leukemia, lymphoma, or myeloma. For example, the hematological malignancy may be acute myeloid leukemia, chronic myelogenous leukemia, childhood acute leukemia, non-Hodgkin's lymphomas, acute lymphocytic leukemia, chronic lymphocytic leukemia, myelodysplastic syndrome, malignant cutaneous T-cells, mycosis fungoids, non-MF cutaneous T-cell lymphoma, lymphomatoid papulosis, and T-cell rich cutaneous lymphoid hyperplasia. In an exemplary embodiment, the patient has a hematological cancer such as acute myelogenous leukemia (AML) or myelodysplastic syndrome, and in some embodiments the patient has relapsed after allogeneic stem cell transplantation. In some embodiments, the therapy does not induce GVHD.

In some embodiments, the patient, in addition to allogeneic stem cell transplantation, has also undergoes lymphodeleting therapy, cyto-reductive therapy, or immunomodulatory therapy (prior to administration of the cell therapy). In some embodiments, the cell therapy may be further provided with or without cytokine support post treatment.

In some embodiments, the patient has an infectious disease or is at risk for an infectious disease. For example, patients that have undergone HSCT are at particular risk for infectious disease, given the immunocompromised state. Infectious diseases that can be treated or prevented include those caused by bacteria, viruses, prions, fungi, parasites, helminths, etc. Such diseases include AIDS, hepatitis B/C, CMV infection, Epstein-Barr virus (EBV) infection, influenza, herpes virus infection (including shingles), and adenovirus infection. CMV, for example, is the most common viral pathogen found in organ transplant patients and is a major cause of morbidity and mortality in patients undergoing bone marrow or peripheral blood stem cell transplants. This is due to the immunocompromised status of these patients, which permits reactivation of latent virus in seropositive patients or opportunistic infection in seronegative individuals. In these embodiments, the patient may receive adoptive immunotherapy comprising T cells specific for pathogen antigens. The method can entail generation of virus-specific CTL derived from the patient or from an appropriate donor before initiation of the transplant procedure.

PTLD occurs in a significant fraction of transplant patients and results from Epstein-Barr virus (EBV) infection. EBV infection is believed to be present in approximately 90% of the adult population in the United States. Active viral replication and infection is kept in check by the immune system, but, as in cases of CMV, individuals immunocompromised by transplantation therapies lose the controlling T cell populations, which permits viral reactivation. This represents a serious impediment to transplant protocols. EBV may also be involved in tumor promotion in a variety of hematological and non-hematological cancers.

In still other embodiments, the invention provides a method for making a population of γδ T cells. The method comprises expanding a population of T cells in the presence of two or more of IL-2, IL-4, IL-6, INF-γ, and IL-1β. The population of T cells may be enriched for CD28+ enriched cells, e.g., may be positively selected with anti-CD28 containing beads or particles, including aAPCs as described herein. In some embodiments, the population of cells is CD4+ depleted or CD8+ selected. In various embodiments, the starting composition comprises less than about 20% or less than about 10% or less than about 8%, or less than about 5% γδ T cells. In some embodiments, source cells are from peripheral blood.

In various embodiments, the population of T cells are expanded in the presence of IL-4, or are expanded in the presence of IL-4 and IL-6. In some embodiments, the cells are expanded in the presence of IL-4 and IL-1β. In some embodiments, the cells are expanded in the presence of IL-4, IL-6, and IL-1β. In some embodiments, the cells are expanded in the presence of IL-2, IL-4, and IL-6. In some embodiments, the cells are expanded in culture in the presence of IL-2, IL-4, IL-6, INF-γ, and IL-1β. Expansion of cells in culture can take place as described herein, such as for 1 to 4 weeks. After the expansion phase, the percent cells that are γδ may be between about 5% and about 60%, such as between about 10% and about 60%, or from about 15% to about 60%, with the numbers of γδ T cells expanded by at least about 100 or at least about 1000, or at least about 10,000, compared to the starting population of cells.

γδ T cells can be separated from other cells using known methods, such as FACS or magnetic cell sorting. γδ T cells can be provided as a cell composition for adoptive transfer or research use, and alternatively may be engineered to express one or more heterologous genes, such as a T cell receptor, which is an optionally an αβ TCR. In some embodiments, the γδ T cells are engineered to heterologously express a chimeric antigen receptor (CAR).

Other aspects and embodiments of the invention will be apparent to the skilled artisan.

EXAMPLES

Figure 2:
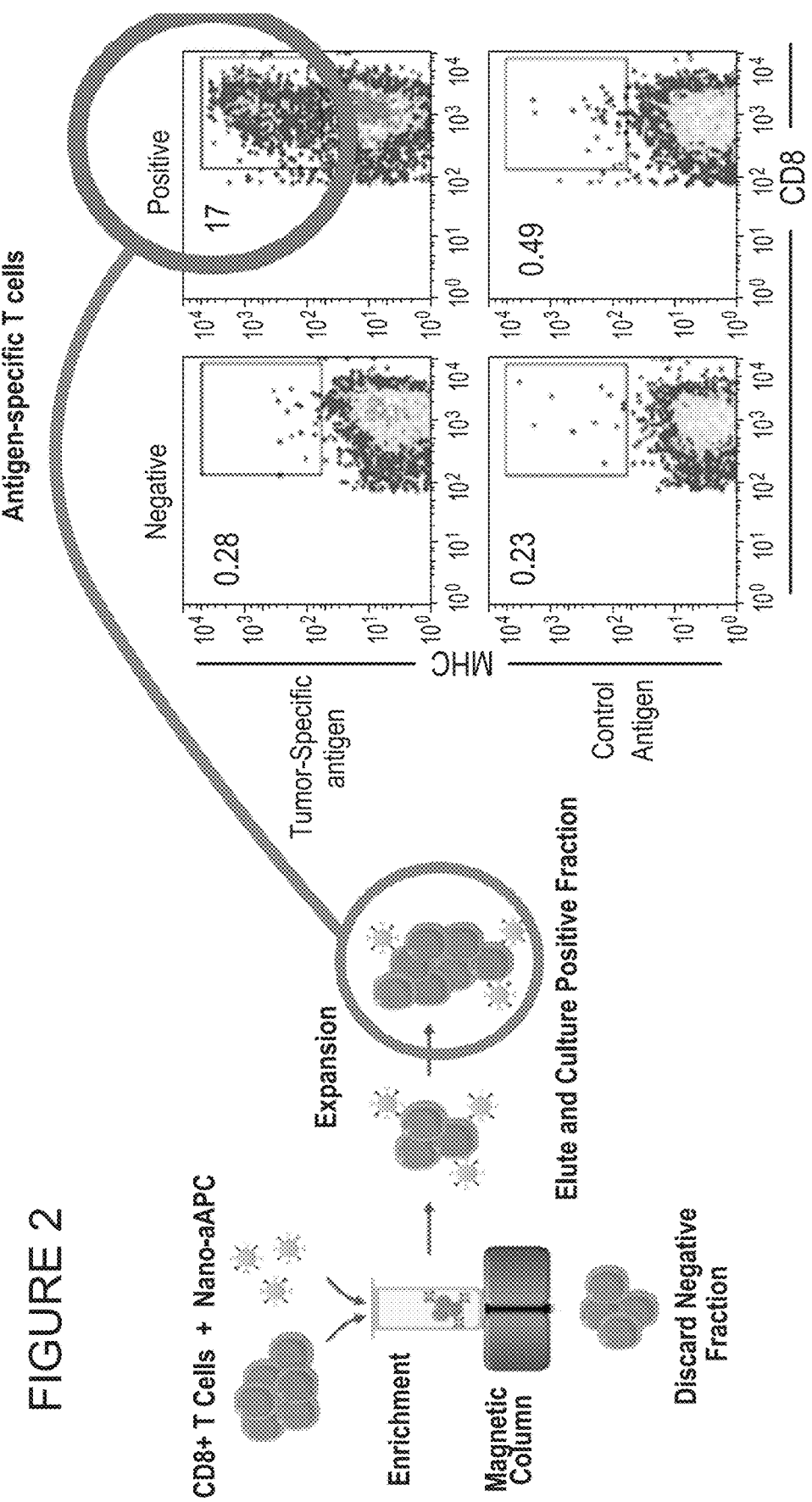
FIG. 2 is an image showing AIM ACT (Adoptive Cellular Therapy) and the Enrichment and Expansion (E+E) cellular expansion system that enables rapid in vitro enrichment and expansion of antigen-specific T cells.

To generate antigen-specific CD8+ T cells, fresh PBMCs were obtained from a donor by leukapheresis, as schematically shown in FIG. 2. Cells were depleted of CD4+ cells by negative selection with anti-CD4 microbeads. Resulting cells were enriched for antigen-specific T cells by incubating with paramagnetic nanoparticles (i.e., dextran-coated iron oxide nanoparticles or PLGA-PEG nanoparticles, ranging in size from about 80-200 nm in diameter). As shown in FIG. 1, the nanoparticles have dimeric HLA ligands conjugated to the surface (presenting the target peptide antigen) that can incorporate multiple tumor specific antigenic peptides. The dimeric HLA ligand contains two HLA-A2 domains, comprising the peptide binding clefts, each fused to an arm of the Ig hinge region. Dimeric HLA-Ig are co-expressed with $\beta_2$ microglobulin. A dimeric HLA ligand, such as an HLA-IgG4 hinge dimer, can be readily modified for multiple HLA-subtypes and provide direct engagement with target T cells. Co-stimulatory or inhibitory ligands, such as an anti-CD28 monoclonal antibody, are also conjugated to the nanoparticle, as shown in FIG. 1. The co-stimulatory or inhibitory ligands provide specific instructions (e.g., activation, suppression) to target T cells (i.e., naïve T cells or memory T cells) relative to the therapeutic goal. Ligands and aAPC constructs are disclosed in WO 2016/044530 and WO 2016/105542, which are hereby incorporated by reference in their entirety.

Cells were incubated in the presence of the paramagnetic aAPC, then in the presence of a magnetic field for about 5 minutes. Cells associated with the particles were then recovered and expanded ex vivo for various lengths of time (generally from 1-2 weeks). Expansion was conducted in the presence of growth factors. For a two-week culture period, growth factors were added on days 1 and 7. Cells were re-stimulated with nano-aAPCs on day 7. Expansion to therapeutic levels of tumor-specific CD8+ T cells was observed within two weeks from donor cell isolation. In some embodiments, the enrichment and expansion process can be performed in an enclosed, automated cellular expansion system. Such a system can provide for simple, scalable, and cost-efficient manufacturing, as well as consistent and rapid generation of antigen-specific CD8+ T cells using different antigen peptide cocktails (i.e., sourced from patient or donor PBMCs).

The composition of the cytokines used for expansion is shown in Table 3.

TABLE 3

| | Cytokines for Expansion Phase | |
|---|---|---|
| Cytokines | Specific Activity in final culture media (IU/ml) | Specific Activity in Stock Solution 50X (IU/ml) |
| IL-2 | 80 | 4000 |
| IL-4 | 2.5 | 250 |
| IL-6 | 160 | 8000 |
| IFNγ | 40 | 2000 |
| IL-1β | 30 | 1500 |

Cell phenotypes using the enrichment and expansion process, including with the expansion phase cytokines, are disclosed in PCT/US2018/051971 (titled CELL COMPOSITIONS COMPRISING ANTIGEN-SPECIFIC T CELLS FOR ADOPTIVE THERAPY). PCT/US2018/051971 is hereby incorporated by reference in its entirety.

Figure 3:
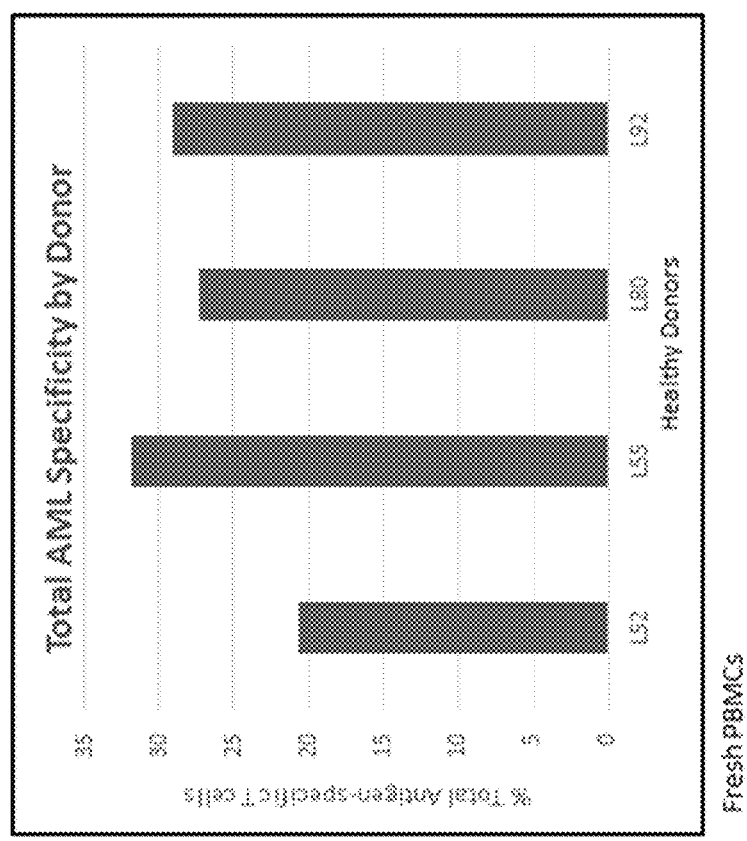
FIG. 3 has two graphs showing the enriched and expanded antigen-specific cell product for the AIM ACT platform. The graph on the left shows the total number of CD8+ T cells generated from fresh PBMCs of four healthy donors after the T cells were enriched and expanded ex vivo for AML-specific antigens $WT1_{37-45, 126-134}$, $PRAME_{425}$, and Cyclin $A1_{227-235, 341-351}$. The graph on the right shows the percentage total of the same acute myeloid leukemia (AML) specific antigens after the CD8+ T cells were enriched and expanded ex vivo.
Figure 3:
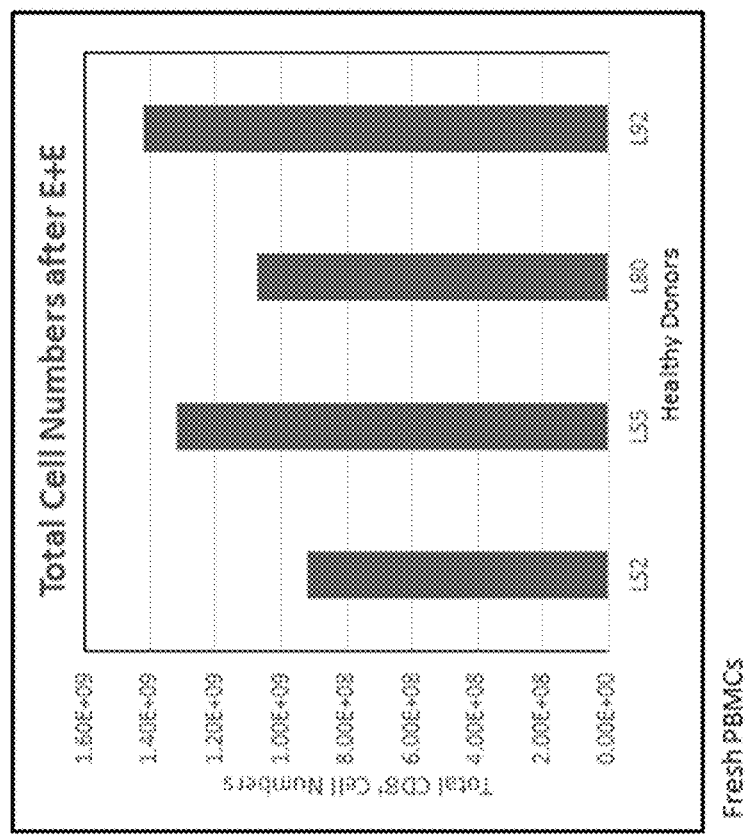

Enrichment and expansion of acute myeloid leukemia (AML)-specific T cells using the methods of the present disclosure are shown in FIG. 3. The graph on the left in FIG. 3 shows the total number of CD8+ T cells generated from fresh PBMCs of four healthy donors after the T cells were enriched and expanded ex vivo for AML-specific antigens $WT1_{37-45}$, $WTI_{126-134}$, $PRAME_{425}$, Cyclin $A1_{227-235}$, and Cyclin $A1_{341-351}$. The graph on the right in FIG. 3 shows the percentage total of the acute myeloid leukemia (AML) specific antigens after the CD8+ T cells were enriched and expanded ex vivo. The results in FIG. 3 demonstrate that a significantly higher proportion of AML-specific CD8+ T cells are generated by the methods of the present disclosure compared to other Endogenous T cell therapy derived cellular compositions.

Figure 4A:
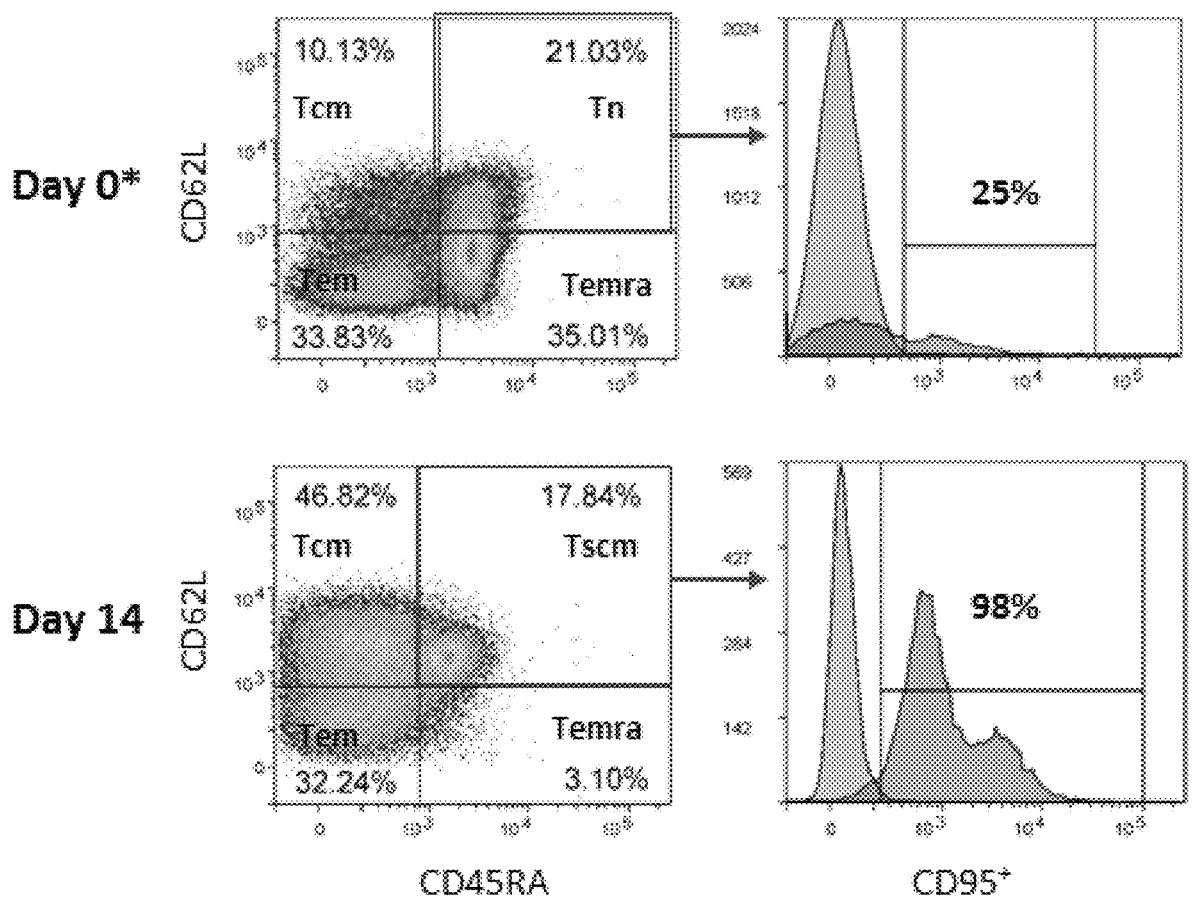
FIG. 4A and FIG. 4B show that the CD8+ T cells generated by the AIM ACT platform comprise memory T cells.
Figure 4B:
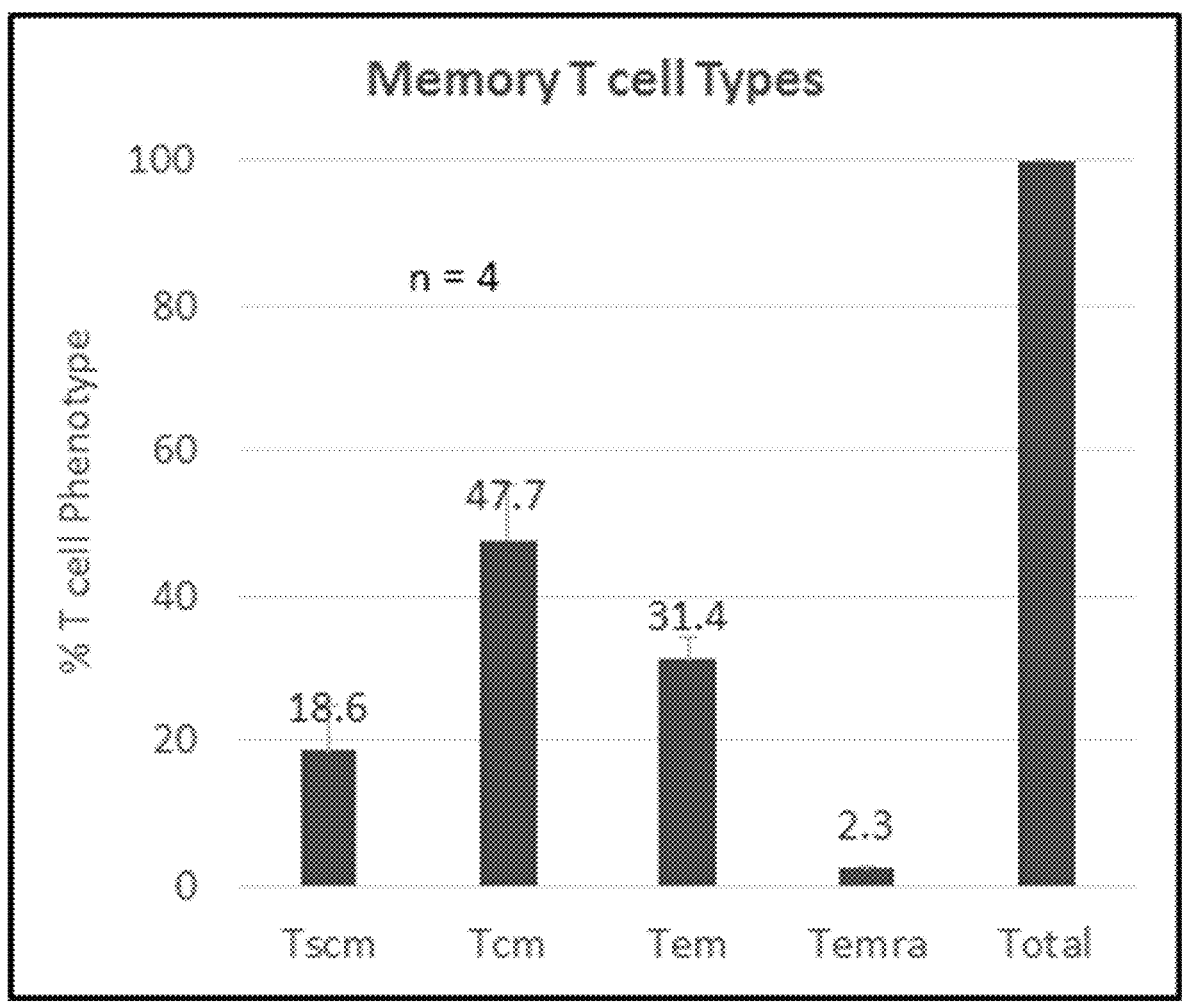

Cells were then characterized in FIG. 4A and FIG. 4B for their phenotype, either naïve T cells ($T_N$) (CD62L+, CD45RA+), central memory T cells ($T_{CM}$) (CD62L+, CD45RA−), effector memory T cells ($T_{EM}$) (CD62L−, CD45RA−), effector memory RA+ T cells ($T_{EMRA}$) (CD62L−, CD45RA+), and T memory stem cells ($T_{SCM}$) (CD62L+, CD45RA+, CD95+). Greater than 95% of the AML specific T cells enriched and expanded ex vivo from donor lymphocytes were of the memory T cell phenotype. Greater than 60% of the E+E generated T cells were of the T memory stem cell phenotype and central memory T cell phenotype. Also, as demonstrated in FIG. 4B, the E+E system generated consistent memory T cell phenotypes across all donors. The E+E process also generated significant amounts of multiple myeloma-specific T memory stem cells from two different healthy donor leucopaks. (See, FIG. 8 and FIG. 9A) In FIG. 9A and FIG. 9B, the multiple myeloma-specific antigenic T cells were enriched and expanded in batch to about ~1.6×10$^9$ CD8+ T cells, based on hinge dimer staining.

Figure 5A:
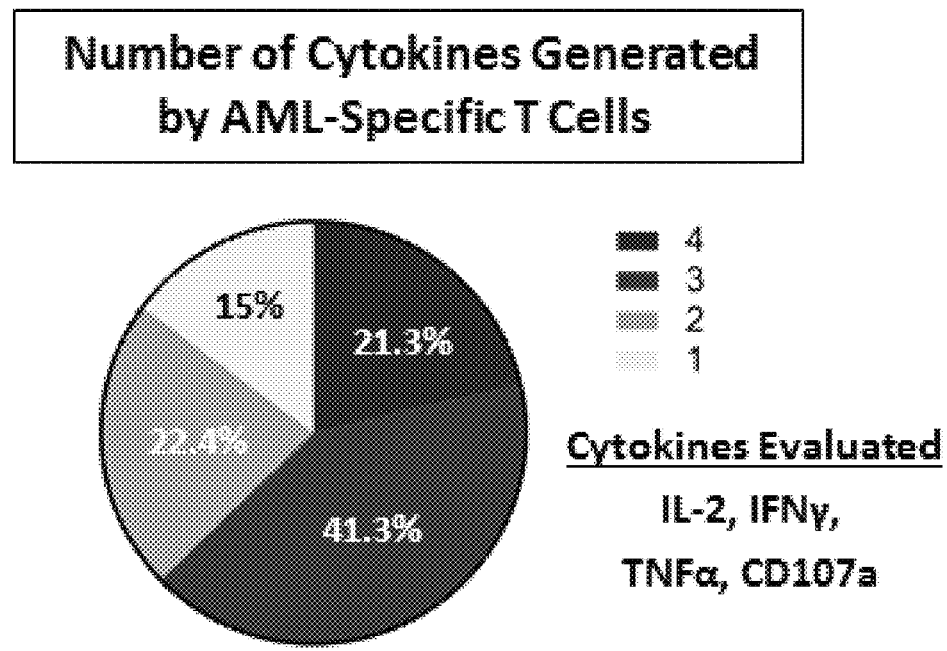
FIG. 5A and FIG. 5B show that AML specific T cells enriched and expanded ex vivo have a high degree of polyfunctional phenotype, including intracellular staining for IL-2 (proliferation and memory), IFN-γ (activating other T cells, memory, upregulation of MHC), TNF-α (pro-inflammatory), and CD107A (granzyme release, cytotoxic activity). The majority of AML-specific T cells (i.e., about 62%) demonstrated 3-4 effector functions upon non-specific stimulation (FIG. 5A, top).
Figure 5A:
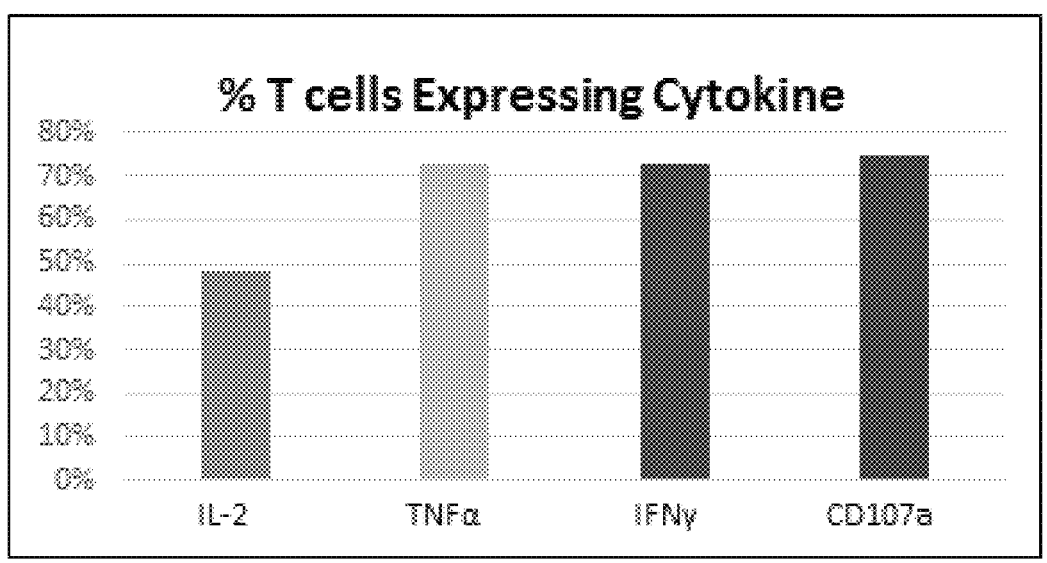
Figure 5B:
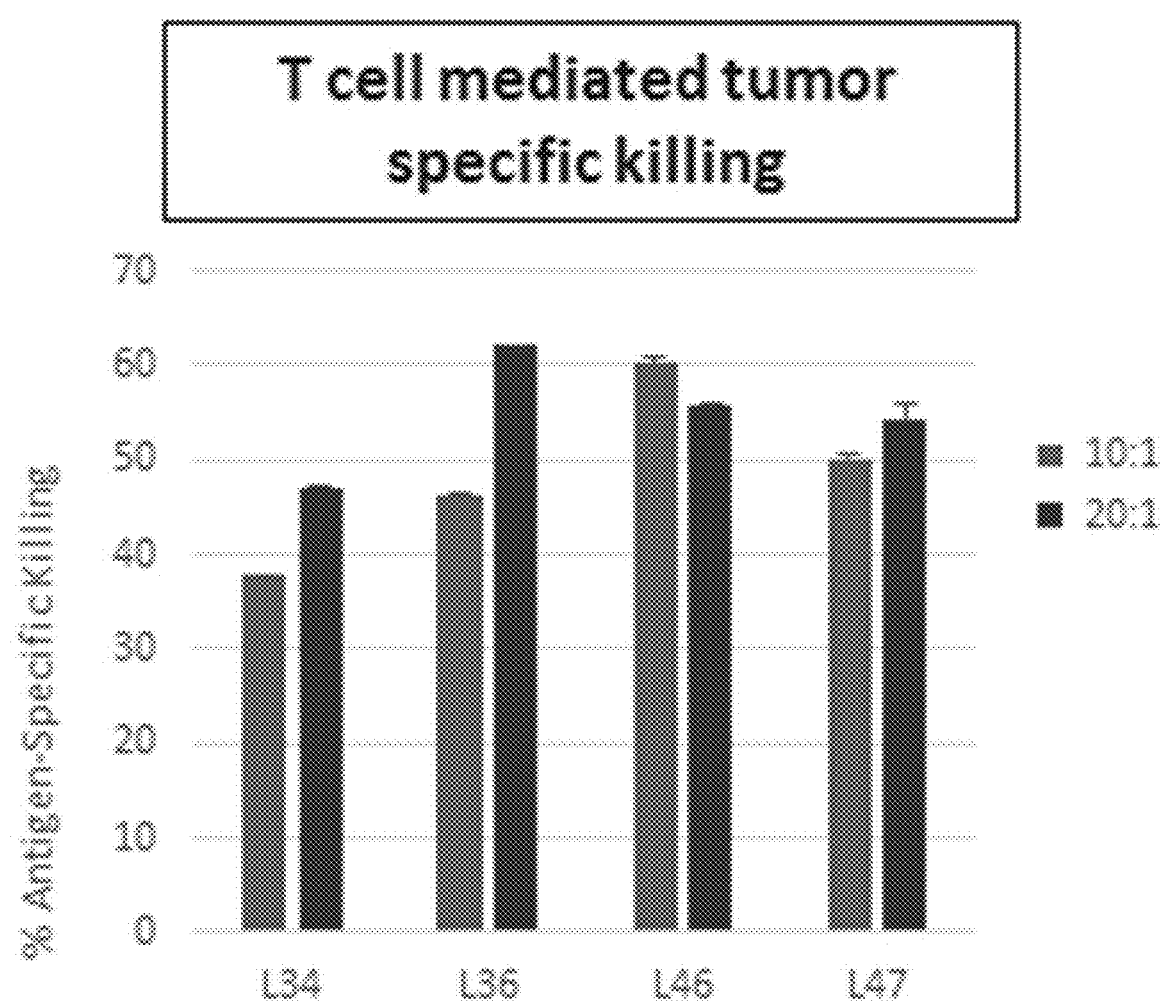

FIG. 5A and FIG. 5B show that AML specific T cells enriched and expanded ex vivo have a high degree of polyfunctional phenotype, including intracellular staining for IL-2 (proliferation and memory), IFN-γ (activating other T cells, memory, upregulation of MHC), TNF-α (pro-inflammatory), and CD107A (granzyme release, cytotoxic activity). The majority of AML-specific T cells (i.e., about 62%) demonstrated 3-4 effector functions upon non-specific stimulation (FIG. 5A, top). In FIG. 5A (bottom), the graph shows the percentage of T cells expressing IL-2, TNF-α, IFN-γ, and CD107A. In FIG. 5A, the T cells were generated by non-specific stimulation of peptide-pulsed T2 cells. The results of this experiment show that for the majority of the E+E generated AML-specific CD8+ T cells, at least 3 or 4 cytokine effector functions were observed. In FIG. 5B, T cell-mediated tumor specific killing of AML cell line U266 is shown at two effector to target (E:T) ratios, 10:1 (left bar) and 20:1 (right bar), from fresh PBMCs of healthy donors for the AML specific antigens. The results of this experiment show that E+E generated CD8+ T cell compositions from healthy donors have a robust killing activity across multiple E:T ratios.

Figure 6:
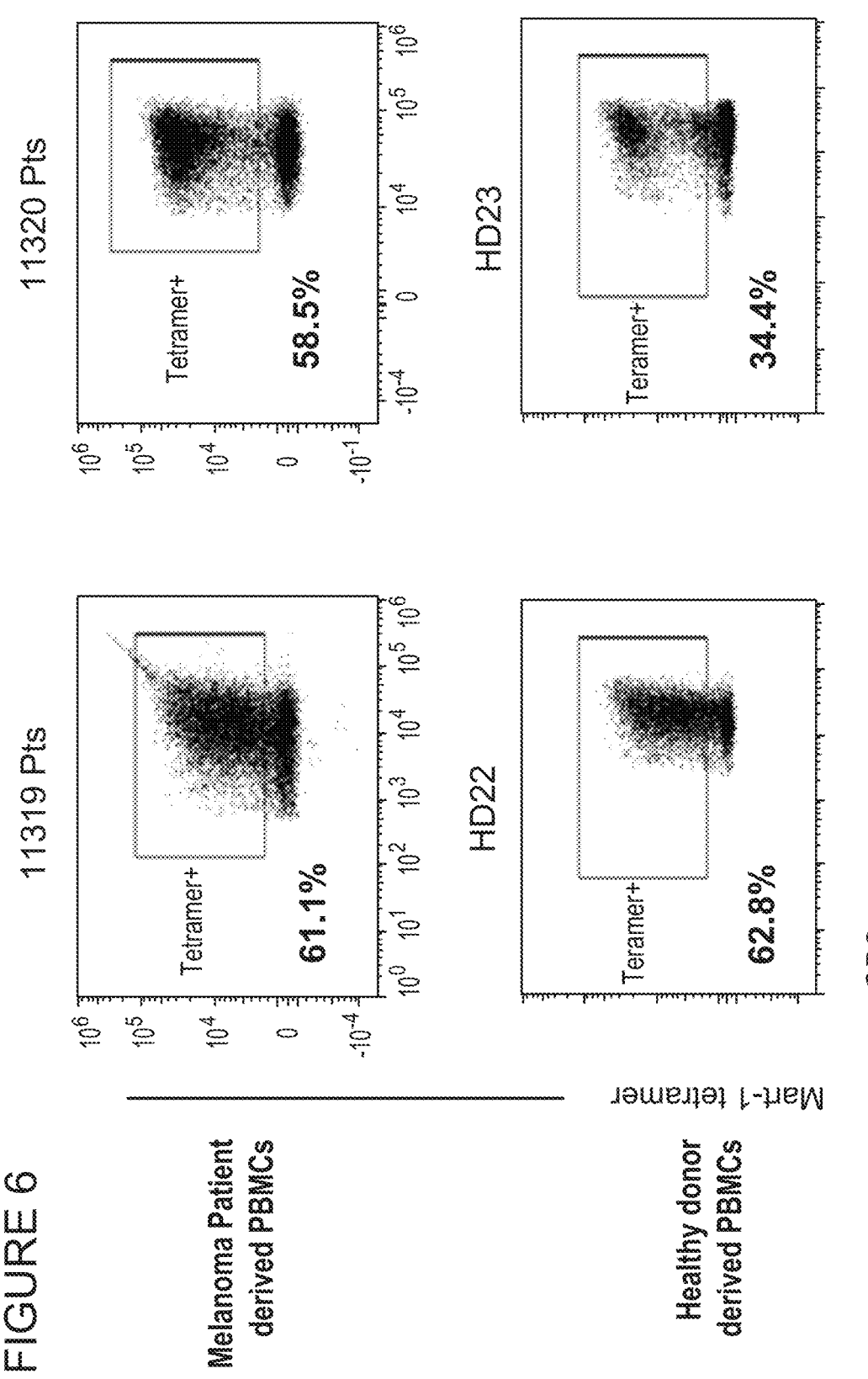
FIG. 6 consists of four graphs comparing the specificity of Mart-1 specific T cells generated by the enrichment and expansion process between melanoma patient derived PBMCs (top) and healthy donor derived PBMCs (bottom). The enrichment and expansion process produces a consistent cellular composition regardless of the donor source. The data in this experiment was generated from frozen PBMCs.

FIG. 6 consists of four graphs comparing the specificity of Mart-1 specific T cells generated by the enrichment and expansion process disclosed herein between melanoma patient derived PBMCs (top) and healthy donor derived PBMCs (bottom). The enrichment and expansion process produces a consistent cellular composition regardless of the donor source. The data in this experiment was generated from frozen PBMCs.

Figure 7:
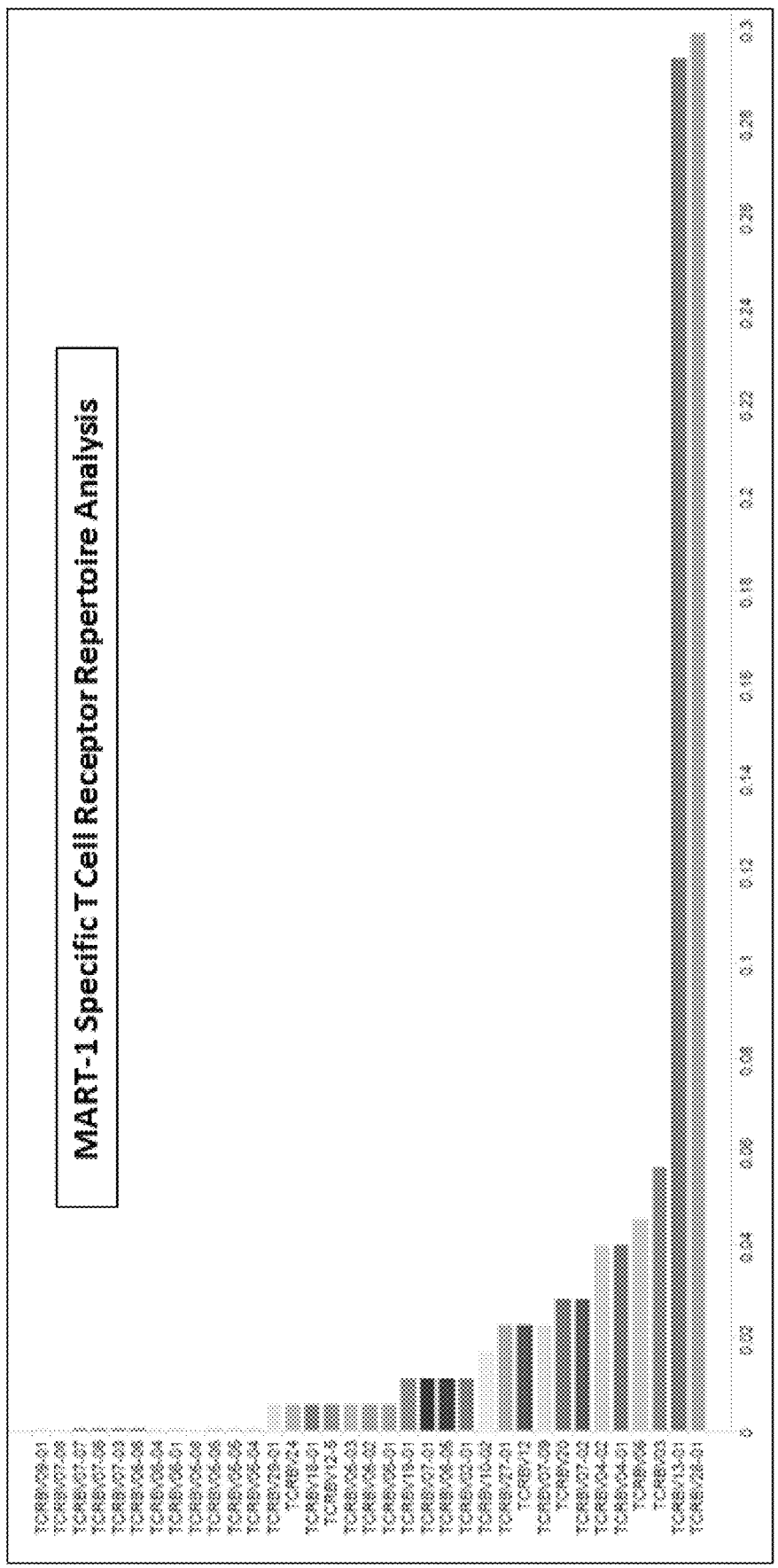
FIG. 7 is a graph showing that the AIM ACT based E+E process generated a TCR repertoire that mimics the natural immune response, thereby providing a robust adoptive therapy from a natural T cell repertoire that has undergone natural selection. The breadth of the polyclonal TCR repertoire enables a natural and durable immune response.

FIG. 7 is a graph showing that the AIM ACT based E+E process generated a TCR repertoire that mimics the natural immune response, thereby providing a robust adoptive therapy from a natural T cell repertoire that has undergone natural selection. The breadth of the polyclonal TCR repertoire enables a natural and durable immune response.

Figure 8:
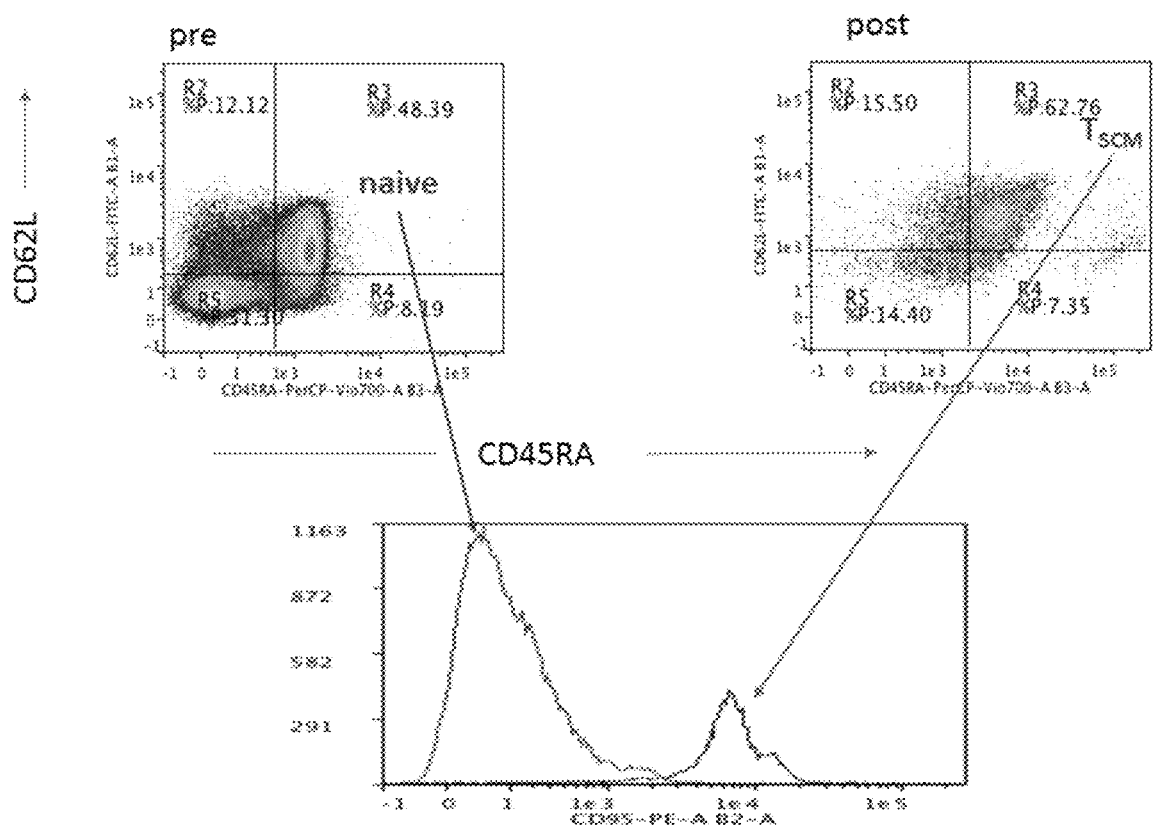
FIG. 8 has graphs showing that the E+E process generated significant amounts of multiple myeloma antigen-specific T memory stem ($T_{SCM}$) cells ((CD62L+, CD45RA+, CD95+). The graphs show the phenotype of multiple myeloma-specific antigenic T cells pre and post expansion from a healthy donor leucopak.
Figure 9A:
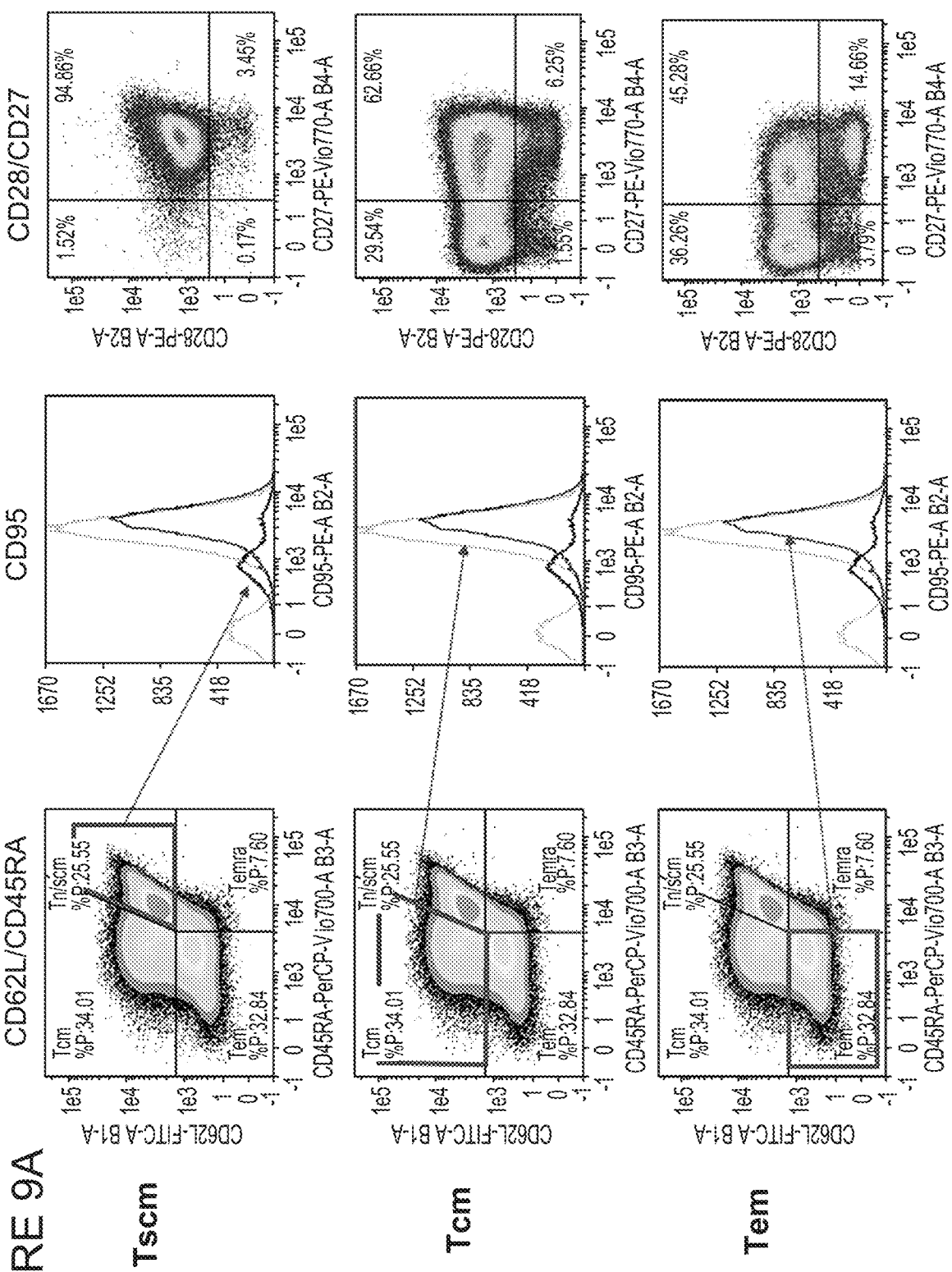
FIG. 9A shows the phenotype of T cells enriched and expanded ex vivo in batch for multiple myeloma antigen-specific T cells from a healthy donor leucopak. The graphs show that the E+E process generated significant amounts of antigen-specific CD8+ T cells (~1.6×10$^9$ CD8+ T cells based on hinge dimer staining) that comprise T memory stem ($T_{SCM}$) cells, central memory T cells $T_{CM}$, and effector memory T ($T_{EM}$) cells.
Figure 9B:
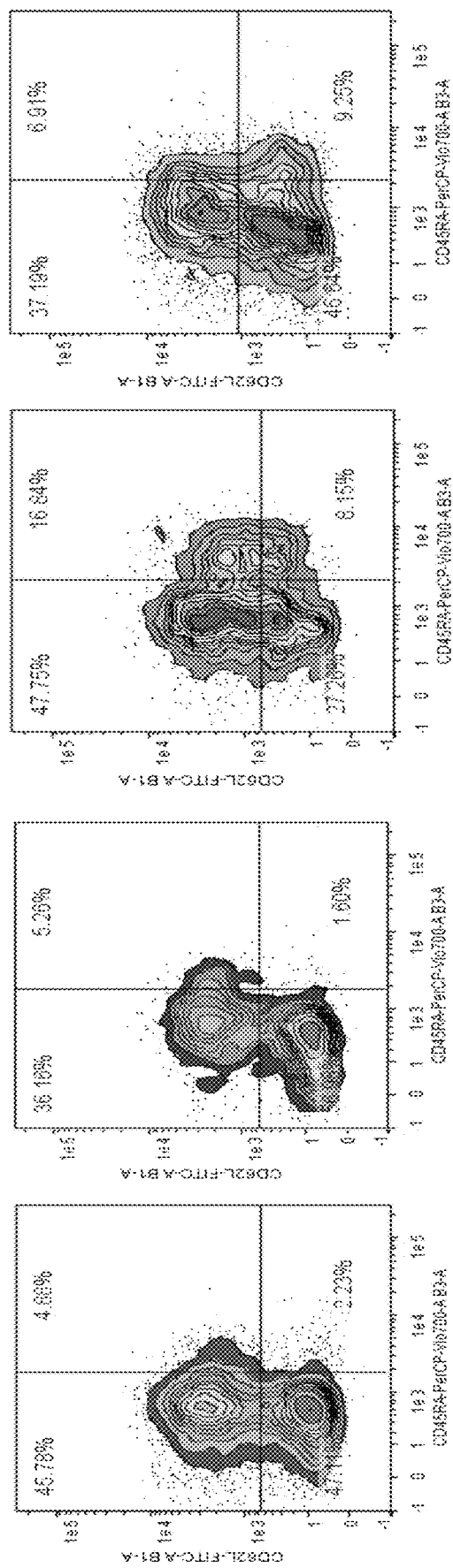
FIG. 9B shows the phenotype of T cells enriched and expanded ex vivo in batch for multiple myeloma antigen-specific T cells from four different clinical multiple myeloma patients. The graphs show that the enrichment and expansion process generated significant amounts of antigen-specific CD8+ T cells that comprise T memory stem ($T_{SCM}$) cells, central memory T cells $T_{CM}$, and effector memory T ($T_{EM}$) cells.

FIG. 8 shows that the E+E process generated significant amounts of multiple myeloma antigen-specific T memory stem (TSCM) cells ((CD62L+, CD45RA+, CD95+). The graphs show the phenotype of multiple myeloma-specific antigenic T cells pre and post expansion from a healthy donor leucopak. FIG. 9A shows the phenotype of T cells enriched and expanded ex vivo in batch for multiple myeloma antigen-specific T cells from a healthy donor leucopak. The graphs show that the E+E process generated significant amounts of antigen-specific CD8+ T cells (~1.6× $10^9$ CD8+ T cells based on hinge dimer staining) that comprise T memory stem (TSCM) cells, central memory T cells TCM, and effector memory T (TEM) cells. FIG. 9B shows the phenotype of T cells enriched and expanded ex vivo in batch for multiple myeloma antigen-specific T cells from four different multiple myeloma patients. The graphs show that the E+E process generated significant amounts of antigen-specific CD8+ T cells that comprise T memory stem ($T_{SCM}$) cells, central memory T cells $T_{CM}$, and effector memory T ($T_{EM}$) cells. This data demonstrates that PBMCs from clinical patients has the same phenotypic characteristics as PBMCs from a donor, and significantly, the E+E process is effective for generating significant amounts of antigen-specific CD8+ T cells that comprise T memory cells (e.g., T memory stem (TSCM) cells, central memory T cells TCM, and effector memory T (TEM) cells).

Figure 10:
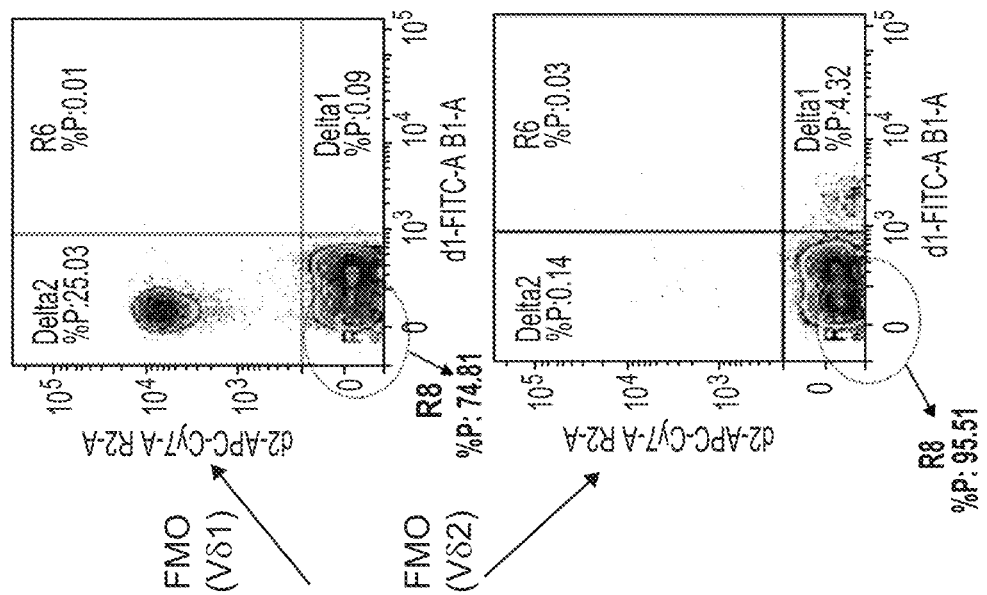
FIG. 10 shows production of γδ T cells, including Vδ1 and Vδ2 TCR subtypes.
Figure 10:
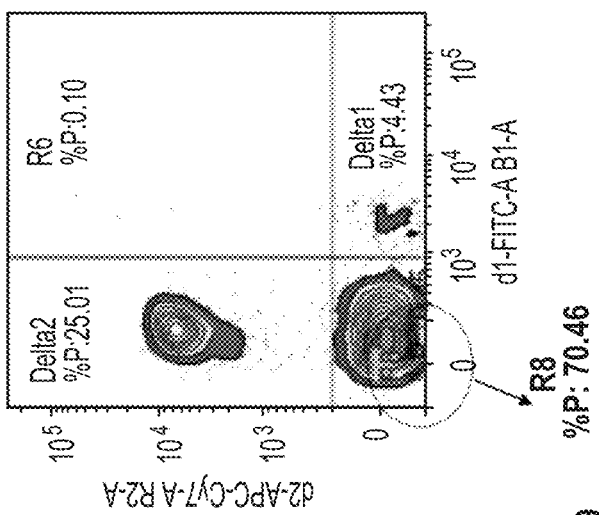
Figure 10:
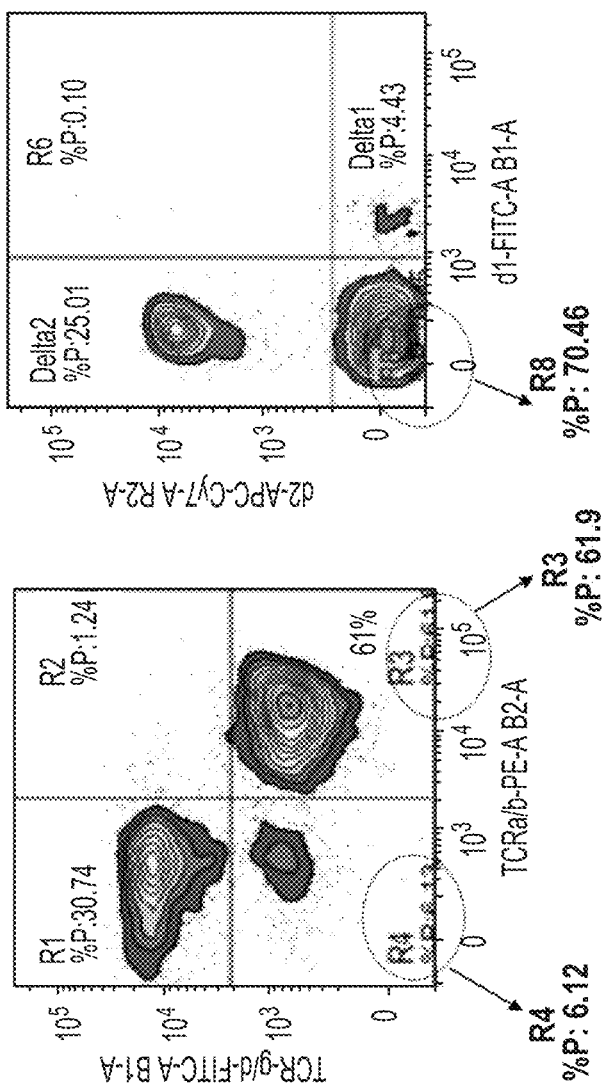
Figure 11:
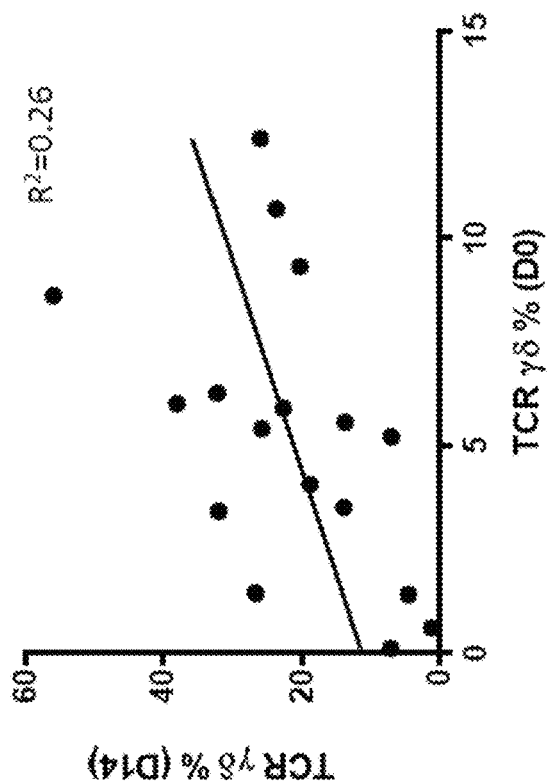
FIG. 11 shows the percent γδ T cells at Day 14, after expanding for various antigen-specific T cells (AML, MM, EBV, MART-1). The percent γδ T cells at Day 14 broadly correlates with the number of γδ T cells at Day 0.
Figure 11:
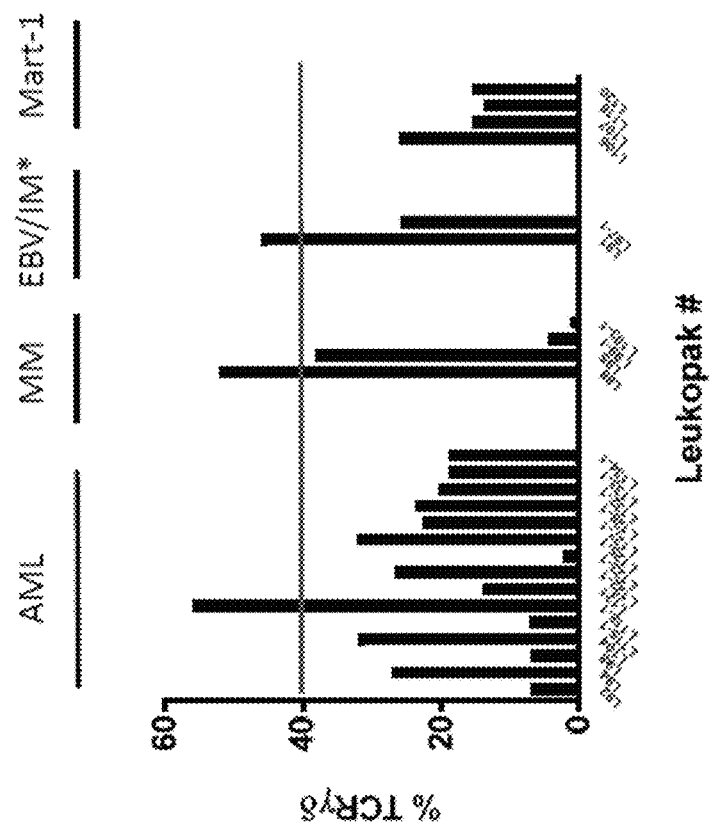

FIG. 10 shows production of γδ T cells using the E+E process. Both Vδ1 and Vδ2 TCR subtypes were observed. The clinical significance of γδ T cells in the context of hematopoietic stem cell transplantation (HSCT) has been reported, and in particular, where higher frequencies of γδ T cells after transplantation are associated with favorable outcomes. See Berglund et al., *Expansion of Gammadelta T cells from Cord Blood: A Therapeutic Possibility.* Stem Cells International Vol. 2018. As shown in FIG. 11, the % γδ T cells at Day 14 varied, with the average being from about 15% to about 50% γδ T cells. The number of γδ T cells at Day 14 broadly correlates with the number of γδ T cells at Day 0.

In the following experiments, characteristics of the expanded T cells are evaluated in terms of identity, purity, phenotype and specificity. Summary characteristics for lots enriched with anti-multiple myeloma (MM) antigen peptides and lots enriched with anti-leukemic antigen peptides are shown below.

TABLE 4

Lot-to-Lot Comparison of Identity Parameters and Contribution of αβ and γδ T Cell Sub-populations*

| Leukopak | % CD3+CD4− | % CD3+/CD8+ | % αβ T cells | % γδ T cells |
|---|---|---|---|---|
| Multiple Myeloma | | | | |
| L163 | 98.1 | 79.5 | 85.8 | 14.6 |
| L165 | 91.2 | 59.8 | 60.5 | 38.9 |
| L179 | 96.6 | 48.3 | 48.9 | 49.5 |
| SV12 | 98.0 | 29.7 | 29.0 | 71.5 |
| SV13 | 98.0 | 42.7 | 37.0 | 59.0 |
| SV14 | 94.5 | 38.8 | 46.7 | 47.4 |
| L136-1 | 93.2 | 87.9 | 89.3 | 4.9 |
| L136-2 | 92.4 | 86.7 | 89.8 | 6.3 |
| L137-1 | 98.3 | 57.0 | 53.5 | 44.0 |
| L137-2 | 98.6 | 58.6 | 55.7 | 42.0 |
| L138-1 | 96.5 | 59.2 | 57.2 | 38.2 |
| L138-2 | 97.2 | 55.7 | 50.6 | 44.4 |
| L144-1 | 93.1 | 89.8 | 90.9 | 3.2 |
| L144-2 | 90.1 | 87.2 | 87.8 | 3.5 |
| L145-1 | 97.0 | 56.0 | 52.4 | 44.0 |
| L145-2 | 98.0 | 63.0 | 60.4 | 39.5 |
| L146-1 | 97.0 | 56.0 | 56.0 | 37.1 |
| L146-2 | 97.0 | 57.0 | 56.0 | 41.3 |
| AML | | | | |
| L162 | 98.7 | 61.9 | 66.4 | 26.4 |
| L164 | 99.2 | 68.8 | 46.5 | 37.8 |
| L167 | 99.6 | 54.1 | 48.8 | 48.6 |
| SV9 | 97.6 | 82.9 | 78.8 | 17.3 |
| SV10 | 86.0 | 30.6 | 38.3 | 41.1 |
| SV11 | 98.5 | 81.4 | 87.1 | 10.0 |
| L132-1 | 94.2 | 72.3 | 69.6 | 20.2 |
| L132-2 | 93.4 | 71.6 | 70.3 | 22.0 |
| L133-1 | 93.2 | 74.3 | 63.5 | 19.7 |
| L133-2 | 92.8 | 75.2 | 64.3 | 17.5 |
| L134-1 | 99.0 | 80.9 | 78.5 | 18.5 |
| L134-2 | 99.3 | 83.6 | 78.3 | 18.9 |
| L140-1 | 97.2 | 41.7 | 33.3 | 65.3 |
| L140-2 | 96.4 | 48.5 | 41.0 | 55.0 |
| L141-1 | 97.5 | 58.0 | 54.0 | 42.7 |
| L141-2 | 99.2 | 57.0 | 52.0 | 45.0 |
| L143-1 | 98.3 | 60.5 | 76.7 | 23.8 |
| L143-2 | 97.7 | 69.0 | 69.1 | 30.3 |
| L147-1 | 95.4 | 68.4 | 60.9 | 37.0 |
| L147-2 | 96.0 | 66.0 | 58.2 | 39.0 |
| L161-1 | 98.4 | 87.7 | 85.0 | 12.9 |
| L161-2 | 98.3 | 86.7 | 85.0 | 12.1 |

*Numbers for CD3+CD8+ and TCR subtype analysis were generated from different samples.
Differences between CD3+CD8+ and αβ T cells are due to different samples and different FCM gating strategies.

In the following experiments, phenotype is the measure of the total % of memory T cells relative to CD3+ cells. The memory T Cell populations characterized include T stem cell memory (Tscm) and T central memory (Tcm) populations, both of which retain the ability to proliferate and self-renew as well as T effector memory (Tem) cells. The remaining populations characterized include Temra and Tnaive cells.

TABLE 5

Lot to Lot Comparison of Phenotype: Tnaive, Tscm, Tcm, Tem, Temra

| Leukopak | Total % Memory T cells | % Tnaive | % Tscm | % Tcm | % Tem | % Temra |
|---|---|---|---|---|---|---|
| Multiple Myeloma | | | | | | |
| L163 | 97.8 | 0.04 | 9.4 | 27.9 | 60.4 | 2.2 |
| L165 | 97.7 | 0.06 | 11.4 | 39.5 | 46.9 | 2.2 |
| L179 | 95.1 | 1.07 | 9.89 | 53.12 | 32.1 | 3.81 |
| SV12 | 99.0 | 0.01 | 11.0 | 41.0 | 47.0 | 1.0 |
| SV13 | 98.0 | 0.90 | 11.0 | 58.0 | 29.0 | 1.8 |
| SV14 | 94.4 | 0.14 | 20.9 | 47.3 | 26.2 | 3.4 |
| L136-1 | 96.26 | 0.2 | 5.06 | 38.7 | 52.5 | 3.54 |
| L136-2 | 95.88 | 0.1 | 4.58 | 37 | 54.3 | 4.02 |
| L137-1 | 92.40 | 4.6 | 5.0 | 33.6 | 53.8 | 3.0 |
| L137-2 | 93.40 | 4.0 | 4.2 | 32.1 | 57.1 | 2.6 |
| L138-1 | 94.78 | 0.6 | 15.4 | 37.82 | 41.56 | 4.65 |
| L138-2 | 95.13 | 0.5 | 16.5 | 40.47 | 38.16 | 5.02 |
| L144-1 | 93.71 | 5.7 | 8.52 | 44.57 | 40.62 | 0.56 |
| L144-2 | 96.91 | 0.7 | 3.3 | 35.15 | 58.46 | 2.37 |
| L145-1 | 96.56 | 0.1 | 3.01 | 38.3 | 55.25 | 3.31 |
| L145-2 | 97.39 | 0.07 | 3.04 | 44.86 | 49.49 | 2.53 |
| L146-1 | 86.91 | 4.42 | 6.58 | 15.18 | 65.15 | 8.67 |
| L146-2 | 88.95 | 3.76 | 3.44 | 8.10 | 77.41 | 7.29 |
| AML | | | | | | |
| L162 | 94.86 | 0.09 | 6.86 | 42.43 | 45.57 | 3.02 |
| L164 | 71.5 | 0.05 | 13.33 | 33.24 | 43.94 | 9.45 |
| L167 | 95.8 | 0.3 | 9.35 | 29.19 | 57.26 | 3.87 |
| SV9 | 98.54 | 0.26 | 6.19 | 57.40 | 34.95 | 1.20 |
| SV10 | 97.89 | 0.43 | 5.73 | 31.88 | 60.28 | 0.70 |
| SV11 | 95.48 | 0.08 | 23.75 | 23.99 | 47.74 | 4.43 |
| L132-1 | 92.82 | 0.2 | 5.34 | 24.3 | 63.18 | 7.17 |
| L132-2 | 93.33 | 0.2 | 5.13 | 22.76 | 65.44 | 6.68 |
| L133-1 | 92.92 | 0.7 | 8.93 | 27.52 | 56.47 | 7.07 |
| L133-2 | 92.97 | 1.1 | 7.66 | 28.43 | 56.88 | 7.03 |
| L134-1 | 94.4 | 0.2 | 3.4 | 11.3 | 79.7 | 5.4 |
| L134-2 | 92.2 | 0.1 | 3.6 | 8.8 | 79.8 | 7.7 |
| L140-1 | 95.8 | 1.8 | 1.6 | 43.7 | 50.5 | 2.4 |
| L140-2 | 96.1 | 1.8 | 1.7 | 42.8 | 51.6 | 2.1 |
| L141-1 | 96.93 | 1.15 | 2.07 | 47.47 | 47.39 | 1.94 |
| L141-2 | 95.22 | 1.85 | 2.33 | 39.13 | 53.76 | 2.92 |
| L143-1 | 93.5 | 0.03 | 6.1 | 24.34 | 63.06 | 6.47 |
| L143-2 | 93.47 | 0.03 | 7.79 | 28.57 | 57.11 | 6.5 |
| L147-1 | 93.8 | 0.34 | 3.4 | 26.5 | 63.9 | 5.8 |
| L147-2 | 94.2 | 0.52 | 3.2 | 23.5 | 67.5 | 5.5 |
| L161-1 | 97.21 | 0.22 | 7.2 | 43.49 | 46.52 | 2.56 |
| L161-2 | 95.97 | 0.13 | 7.3 | 34.86 | 53.81 | 3.9 |

As demonstrated by the experiments described above, the CD8+ T cell compositions disclosed herein directly engage with T cell receptors on naïve and memory T cells to trigger a desired immune response. The CD8+ T cell compositions, which are generated by the enrichment and expansion process are composed of a multi-antigen specific, CD8+ restricted, T cells from an endogenous repertoire. The antigen-specific CD8+ T cell composition includes T memory stem cells. T memory stem cells and central memory T cells are instrumental and critical for both initial and long-term clinical responses. The antigen-specific CD8+ T cell composition have a polyfunctional phenotype, as assessed by effector cytokine production and target cell killing. The E+E process also generated a natural immune response driven by a diverse TCR repertoire. In addition to the robust population of αβ T cells, a significant population of γδ T cells were also present in the expanded population, which included both Vδ1 and Vδ2 cells. γδ T cells are believed to provide additional mechanisms of pathogen or cancer cell killing, which are not HLA dependent.

The invention claimed is:

1. A method for producing a cell composition comprising CD8+ cytotoxic T lymphocytes (CTLs) specific for one or more cancer-associated peptide antigens for adoptive immunotherapy, comprising:
providing a sample of T cells from whole blood or buffy coat fraction, bone marrow, lymph node tissue, spleen tissue, or tumor;
depleting the sample of CD4+ T cells;
expanding the CD4+ depleted cells ex vivo in the presence of cytokines consisting of IL-2, IL-4, IL-6, INF-γ, and IL-1β, and in the presence of artificial Antigen Presenting Cells (aAPCs) presenting one or more cancer-associated peptide antigens through association with HLA ligands, the aAPCs further presenting T lymphocyte co-stimulatory ligands;
wherein after expansion, the CD8+ T cells in the composition are predominately central memory ($T_{cm}$) and effector memory ($T_{EM}$) phenotype, and comprise T memory stem cells; and at least 15% of the T cells in the composition are specific for the cancer-associated peptide antigen.

2. The method of claim 1, wherein the CD4+ depleted cells are expanded in the presence of a population of artificial Antigen Presenting Cells (aAPCs) comprising HLA ligands presenting from 1 to 10 cancer-associated peptide antigens.

3. The method of claim 2, wherein the population of aAPCs comprise HLA ligands presenting at least 3 cancer-associated peptide antigens.

4. The method of claim 2, wherein the aAPCs comprise a paramagnetic core, and the population of cells are activated in the presence of a magnetic field for a duration of from 2 to 30 minutes.

5. The method of claim 4, wherein the population of CD4+ depleted cells are enriched for T cells specific for said cancer-associated peptide antigens by magnetic enrichment with the paramagnetic aAPCs.

6. The method of claim 1, wherein the T lymphocyte co-stimulatory ligands are CD28 agonists.

7. The method of claim 1, wherein said cancer-associated peptide antigens are associated with acute myelogenous leukemia or multiple myeloma.

8. The method of claim 7, wherein said cancer-associated peptide antigens comprise epitopes derived from one or more of SURVIVIN, WT-1, PRAME, RHAMM, PR3, and CYCLIN A1.

9. The method of claim 7, wherein said cancer-associated peptide antigens comprise epitopes derived from one or more of NY-ESO-1, WT-1, SOX-2, CD138, CS1, XBP1-US, and XBP1-SP.

10. The method of claim 1, wherein the cell composition has at least 70% central and effector memory T cells.

11. The method of claim 10, wherein the cell composition has at least 80% central and effector memory T cells.

12. The method of claim 1, wherein the cell composition has less than 10% terminally differentiated T cells.

13. The method of claim 1, wherein the cell composition has less than 5% naive cells.

14. The method of claim 1, wherein the cell composition has from 1% to 25% T memory stem cells.

15. The method of claim 1, wherein at least 30% of the CD8+ T cells in the composition are specific for the cancer-associated peptide antigens.

16. The method of claim 1, wherein at least 50% of the CD8+ T cells in the composition are specific for the cancer-associated peptide antigens.

17. The method of claim 1, wherein the cell composition further comprises γδT cells.

18. The method of claim 1, wherein the cell composition comprises at least 10% γδT cells.

19. The method of claim 1, wherein the cell composition comprises at least $10^7$ CD8+ T cells specific for the cancer-associated peptide antigens.

20. The method of claim 1, wherein the population of cells is expanded in culture for from 1 to 4 weeks.

21. The method of claim 20, wherein the population of cells is expanded in culture for about 2 weeks.

* * * * *